US008115014B2

(12) United States Patent
Ohmoto et al.

(10) Patent No.: US 8,115,014 B2
(45) Date of Patent: Feb. 14, 2012

(54) ETHYNYLINDOLE COMPOUNDS

(75) Inventors: Kazuyuki Ohmoto, Osaka (JP); Satoshi Itadani, Osaka (JP); Yoshisuke Nakayama, Osaka (JP); Jun Takeuchi, Osaka (JP); Manabu Fujita, Osaka (JP)

(73) Assignee: ONO Pharmaceuticals, Co., Ltd., Osaka (JP)

( * ) Notice: Subject to any disclaimer, the term of this patent is extended or adjusted under 35 U.S.C. 154(b) by 0 days.

(21) Appl. No.: 12/644,378

(22) Filed: Dec. 22, 2009

(65) Prior Publication Data

US 2010/0160647 A1    Jun. 24, 2010

(30) Foreign Application Priority Data

Dec. 22, 2008   (JP) ................ 2008-325815

(51) Int. Cl.
C07D 209/04     (2006.01)
A61K 31/405    (2006.01)
A61K 31/40     (2006.01)
(52) U.S. Cl. ............ 548/491; 514/415; 514/419
(58) Field of Classification Search .............. None
See application file for complete search history.

(56) References Cited

U.S. PATENT DOCUMENTS

| | | | |
|---|---|---|---|
| 5,137,910 | A | 8/1992 | Gray et al. |
| 5,229,413 | A | 7/1993 | Gray et al. |
| 5,530,019 | A | 6/1996 | Okada et al. |
| 5,965,745 | A | 10/1999 | Brown et al. |
| 6,057,317 | A | 5/2000 | Guillaumet et al. |
| 6,833,387 | B1 | 12/2004 | Faull et al. |
| 7,728,023 | B2 * | 6/2010 | Takeuchi et al. ............... 514/381 |
| 2006/0194797 | A1 | 8/2006 | Takeuchi et al. |
| 2008/0188532 | A1 | 8/2008 | Takeuchi et al. |

FOREIGN PATENT DOCUMENTS

| | | |
|---|---|---|
| AU | 2004 268865 | 3/2005 |
| EP | 0 405 116 | 1/1991 |
| EP | 1 661 892 | 5/2006 |
| EP | 1 852 420 | 11/2007 |
| JP | 01-192476 | 8/1989 |
| JP | 11-092476 | 8/1989 |
| JP | 11--92476 | 8/1989 |
| JP | 03 047123 | 2/1991 |
| JP | 07 507574 | 8/1995 |
| JP | 10 512291 | 11/1998 |
| JP | 2002-536362 | 10/2002 |
| JP | 20 025362 | 7/2003 |
| WO | WO-02 000646 | 1/2002 |
| WO | WO-03 074051 | 9/2003 |
| WO | WO-03 082271 | 10/2003 |
| WO | WO-03/091215 A1 | 11/2003 |
| WO | WO-2004/007451 A1 | 1/2004 |
| WO | WO-2004 099192 | 11/2004 |
| WO | WO-2005 021518 | 3/2005 |
| WO | WO-2006 090817 | 8/2006 |

OTHER PUBLICATIONS

English Abstract of JP-2002-536362, Publication Number: Oct. 29, 2009, Data supplied from the espacenet database—Worldwide on Jul. 20, 2010.
Office Action dated May 26, 2010 for the Israeli Patent Application No. 185199.
English Translation of Office Action dated May 26, 2010 for the Israeli Patent Application No. 185199.
Australian Office Action for related Patent Application No. 2006 216170 dated Jan. 5, 2011.
English Translation of Decision on Rejection for Chinese Patent Application No. 200680005791 dated Oct. 12, 2010.
English Translation of Second Office Action for Russian Patent Application No. 2007135347/04(038646) dated May 12, 2010.
Office Action for Japanese Patent Application No. 2005 513507dated Jun. 22, 2010.
Second Office Action for European Patent Application No. 04772519.7-2117 dated Aug. 9, 2010.
Second Office Action for Russian Patent Application No. 2007135347/04(038646) dated May 12, 2010.
Third Office Action for related Chinese Patent Application No. 2004 80025056 dated Dec. 14, 2010.
Kawasaki Steel Corp., "Manufacture of Welded Steel Pipe," Patent Abstract of Japan, Publication Date: Aug. 2, 1989; English Abstract of JP-01-192476.

(Continued)

*Primary Examiner* — Kamal Saeed
*Assistant Examiner* — Nyeemah A Grazier
(74) *Attorney, Agent, or Firm* — Millen, White, Zelano & Branigan, P.C.

(57) ABSTRACT

As a compound having a potent oral activity and a long-lasting $cysLT_1/cysLT_2$ receptor antagonistic activity, the compound of the formula (I):

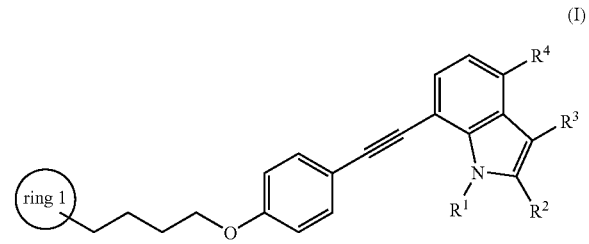

which exhibits potent antagonistic activity against the $cysLT_1/cysLT_2$ receptor, and have long-lasting effects even in case of oral administration, and therefore is useful as an oral agent for preventing and/or treating a variety of diseases, for example, respiratory disease (for example, asthma (bronchial asthma, etc.), chronic obstructive pulmonary disease (COPD), pulmonary emphysema, chronic bronchitis, pneumonia (interstitial pneumonia, etc.), severe acute respiratory syndrome (SARS), acute respiratory distress syndrome (ARDS), apnea syndrome, allergic rhinitis, sinusitis (acute sinusitis, chronic sinusitis, etc.), pulmonary fibrosis, coughing (chronic coughing, etc.), and the like) was developed.

8 Claims, 3 Drawing Sheets

OTHER PUBLICATIONS

European Search Report for European Application No. 09180244 dated Apr. 26, 2010.

Office Action dated Feb. 3, 2010 for the Israeli Patent Application No. 173898.

English Translation of Office Action dated Feb. 3, 2010 for the Israeli Patent Application No. 173898.

Julia, M. et al., "No. 386.—Recherches en serie indolique. VII.—Sur la Cyclisation des alpha-arylaminocetones," Bulletin de la Societe Chimique de France, 1962, pp. 2263-2267.

Lenzi et al., "A series of alpha-arylamino ketones was cyclized by simple heating to the corresponding indoles," STN Tokyo, 1963; English Translation of Julia, M. et al., "No. 386.—Recherches en serie indolique. VII.—Sur la Cyclisation des alpha-arylaminocetones," Bulletin de la Societe Chimique de France, 1962, pp. 2263-2267.

Daines, Robert A. et al., "First X-ray Cocrystal Structure of a Bacterial FabH Condensing Enzyme and a small Molecule Inhibitor Achieved Using Rational Design and Homology Modeling," J. Med. Chem., 2003, vol. 46, pp. 5-8.

Rajur, Sharanabasava B. et al., "Synthesis of 1,2,3,4-tetrahydropyrazino-[1,2-a] indoles and ethyl 1-(2-amino-ethyl) indole-2-carboxylates," Indian Journal of Chemistry, Dec. 1989, vol. 28B, pp. 1065-1068.

Basanagoudar, L. D. et al., "Synthesis of 10-phenyl-1,2,3,4-tetrahydropyrazino[1,2-a]indoles and ethyl 1-(2-aminoethyl)-3-phenylindole-2-carboxylates," Indian Journal of Chemistry, Nov. 1991, vol. 30B, pp. 1014-1017.

Salituro, Francesco G. et al., "3-(2-Carboxyindol-3-yl) propionic Acid-Based Antagonist of the N-Methyl-D-aspartic Acid Receptor Associated Glycine Binding Site," J. Med. Chem., 1992, vol. 35, pp. 1791-1799.

Di Fabio, R. et al., "Substituted Indole-2-carboxylates as in Vivo Potent Antagonists Acting as the Strychnin-Insensitive Glycine Binding Site," J. Med. Chem., 1997, vol. 40, pp. 841-850.

Heinrich, T et al., "A New Synthesis of indole 5-carboxylic acids and 6-hydroxy-indole-5-carboxylic acids in the preparation of an o-hydroxylated metabolite of vilazodonem," Bioorganic & Medicinal Chemistry Letters, 2004, vol. 14, pp. 2681-2684.

Stella, Valentino J., "Prodrugs as therapeutics," Expert Opin. Ther. Patents, 2004, vol. 14, No. 3, pp. 277-280.

Wolff, Manfred E., "vol. 1: Principles and Practice," Burger's Medicinal Chemistry and Drug Discovery: Fifth Edition, Mar. 16, 1995.

Testa, Bernard, "Prodrug research: Futile or Fertile?" Biochemical Pharmacology, 2004, vol. 68, pp. 2097-2106.

Ettmayer, Peter et al., "Lessons Learned from Marketed and Investigational Prodrugs," Journal of Medicinal Chemistry, May 6, 2004, vol. 47, No. 10.

Vippagunta, Sudha R. et al., "Crystalline solids," Advanced Drug Delivery Reviews, 2001, vol. 48, pp. 3-26.

Morissette, Sherry L. et al., "High-throughput crystallization: polymorphs, salts, co-crystals and solvates of pharmaceutical solids," Advanced Drug Delivery Reviews, 2004, vol. 56, pp. 275-300.

Touzeau, F. et al., "Synthesis and Biological Evaluation of New 2-(4,5-Dihydro-1H-imidazol-2-yl)-3,4-dihydro-2H-1,4-benzoxazine Derivatives," J. Med. Chem., 2003, vol. 46, pp. 1962-1979.

Mayer, Stanislas et al., "Regioselective formylation of ethyl 3,4-dihydro-2H-1,4-Benzoxazine-2-Carboxylate or 2-acetate derivatives," Heterocycles, 2001, vol. 55, No. 10.

West, A. R., "Solid State Chemistry and its applications," Mar. 3, 1988, Wiley, New York.

Non-Final Rejection in Related U.S. Appl. No. 10/569,482 dated Feb. 11, 2009.

Non-Final Rejection in Related U.S. Appl. No. 10/569,482 dated Oct. 13, 2009.

Office Action for Russian Patent Application No. 2007135347/04 (038646), Feb. 3, 2010.

Office Action for New Zealand Patent Application No. 560513, Jul. 9, 2009.

Office Action for Chinese Patent Application No. 200680005791.0, Sep. 18, 2009.

Office Action for European Patent Application No. 04772519.7-2117, Jan. 2, 2010.

Office Action for Russian Patent Application No. 2006110513/04 (011450), Jul. 5, 2008.

Office Action for New Zealand Patent Application No. 545666, Dec. 5, 2008.

Office Action for Autstralian Patent Application No. 2004268865, Nov. 12, 2009.

First Office Action for Chinese Patent Application No. 200480025056, Feb. 22, 2008.

Second Office Action for Chinese Patent Application No. 200480025056.7, Jan. 22, 2010.

Office Action for Indian Patent Application No. 756/KOLNP/2006, Oct. 2, 2009.

Third Office Action for related European Patent Application No. 04 772 519 dated Mar. 23, 2011.

Office Action for realted Canadian Patent Appliation No. 2 537 355 dated Mar. 28, 2011.

Office Action from U.S. Appl. No. 11/885,018.

Kawasaki Steel Corp., "Manufacture of Welded Steel Pipe," Patent Abstract of Japan, Publication Date: Aug. 2, 1989; English Abstract of JP-11-092476.

Office Action for Chinese Patent Application No. 200910260865 dated Sep. 7, 2011.

English Translation of Office Action for Chinese Patent Application No. 200910260865 dated Sep. 7, 2011.

* cited by examiner

ETHYNYLINDOLE COMPOUNDS

TECHNICAL FIELD

The present invention relates to a compound of the formula (I):

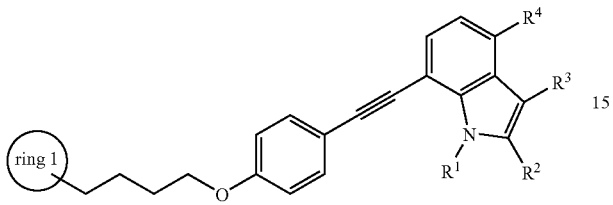

wherein all the symbols have the same meanings as defined hereinafter.

BACKGROUND ART

Bronchial asthma is a pathological condition where the airway is constricted by airway contraction or inflammation, which causes paroxysmal coughing, stridor, and dyspnea. Therapeutic agents for bronchial asthma include inhaled corticosteroids, which have potent anti-inflammatory effects, β stimulants and theophyllines which are bronchodilating agents, and agents which inhibit the activity of chemical mediators, etc.

Histamines, leukotrienes, prostaglandins, and the like are known as chemical mediators which are released from mast cells or inflammatory cells which are involved in bronchial asthma. Among leukotrienes (LTs), cysteinyl leukotrienes (hereinafter, referred to as "cysLTs") represented by $LTC_4$, $LTD_4$ and $LTE_4$ have an approximately 1,000-fold stronger airway contractile effect as compared to histamine. Moreover, cysLTs promote induction of airway inflammation, typically by inflammatory cell infiltration, airway hypersensitivity and mucus secretion in the airway, by which they are deeply involved in the underlying pathological condition of bronchial asthma.

CysLTs are physiologically active substances in vivo which are 5-lipoxygenase metabolites of arachidonic acid. There are at least two different types of receptors for cysLTs, and a $cysLT_1$ receptor and a $cysLT_2$ receptor have been cloned to date (Nature, 399, 789-793, 1999, *J. Biol., Chem.*, 275, 30531-30536, 2000). The $cysLT_1$ receptor is expressed primarily in airway smooth muscle, and deeply relates to the onset of bronchial asthma (Am. J. Respir. Crit. Care Med., 163, 226-233, 2001). Meanwhile, it has been reported that the $cysLT_2$ receptor adopts $LTC_4$, $LTD_4$, and $LTE_4$ as a ligand, similar to the $cysLT_1$ receptor, and is expressed in bronchial smooth muscle (*J. Biol. Chem.*, 275, 30531-30536, 2000, *Am. J. Respir. Crit. Care Med.*, 164, 2098-2101, 2001).

Pranlukast hydrate, Montelukast sodium and Zafirlukast are currently commercially available leukotriene receptor antagonists, and they are used as an oral drug for treating bronchial asthma and/or an oral drug for treating allergic rhinitis.

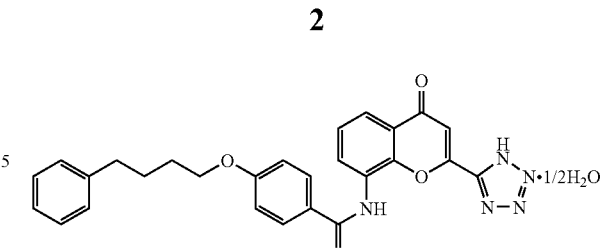

Pranlukast hydrate

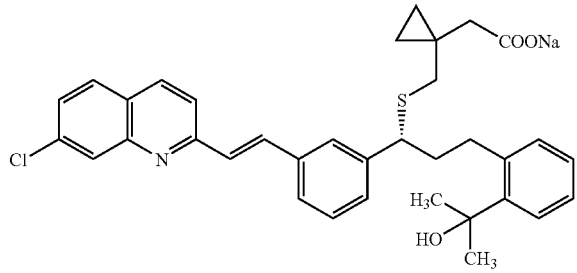

Montelukast sodium

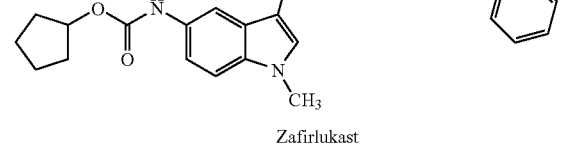

Zafirlukast

However, it is known that these leukotriene receptor antagonists are more effective for mild or moderate bronchial asthma than for severe ones. It is also known that there exist some non-responders whom the pharmaceutical agent does not have sufficient effects in mild or moderate bronchial asthma. Accordingly, there has been a demand for agents having a higher therapeutic activity than the existing agents.

One of the means for accomplishing the object is to enhance a leukotriene receptor antagonistic activity of the agents. The currently commercially available three compounds are all $cysLT_1$ antagonists. As approaches to potentiate the receptor antagonistic activity, a method of further enhancing a $cysLT_1$ antagonistic activity and a method of constructing a combination of $cysLT_1$ antagonistic activity and $cysLT_2$ antagonistic activity are devised.

Meanwhile, antiasthmatic drugs are required to be medicated on a regular basis and therefore oral preparations are preferred which are convenient for taking medicine. Among oral preparations, drugs with less dosing frequencies are preferred for convenience of medication. Namely, an oral anti-asthma drug is preferred having a long-term activity. With regard to development of oral preparations, it is very important to improve the duration of drug efficacy.

However, particularly in oral preparations, a compound that is of interest per se may be labile; may exhibit poor delivery to the target organ; or may exhibit early metabolism and excretion even though an antagonistic activity of the compound is potent. For these reasons, it is not easy to obtain a compound having long-lasting potent effects.

WO2005/021518 (Patent Document 1) discloses that a compound of the formula (A):

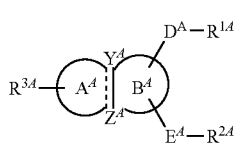

wherein $R^{1A}$ and $R^{2A}$ each independently represent a group having an acidic group which may be protected, $D^A$ and $E^A$ each independently represent a bond or a spacer which has a main chain having 1 to 8 atoms, $R^{3A}$ represents a substituent, ring $A^A$ represents a cyclic group which may further have substituent(s), ring $B^A$ represents a cyclic group which may further have substituent(s), $Y^A$ and $Z^A$ each independently represent a carbon atom or a nitrogen atom, and ――――― represents a single bond or a double bond, wherein when $Y^A$ and/or $Z^A$ represents a nitrogen atom, the bond represents a single bond, has cysLT$_2$ receptor antagonistic effects.

However, there is no disclosure or suggestion of which ring specifically contributes to the duration of drug efficacy, even though a variety of ring-fused compounds are disclosed therein.

WO2006/090817 (Patent Document 2) discloses that a compound of the formula (B):

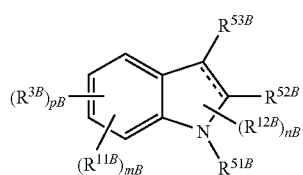

wherein $R^{11B}$ and $R^{12B}$ each independently represents a substituent, two groups selected from $R^{51B}$, $R^{52B}$ and $R^{53B}$ each independently represent a group having an acidic group which may be protected, the other one of $R^{51B}$, $R^{52B}$ and $R^{53B}$ represents a hydrogen atom or a substituent, $R^{3B}$ represents

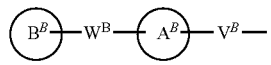

(wherein $V^B$ and $W^B$ each independently represent a bond or a spacer which has a main chain having 1 to 8 atoms, and ring $A^B$ and ring $B^B$ each independently represent a cyclic group which may have substituent(s)) or the like, mB represents 0 or an integer of 1 to 4, nB represents 0 or an integer of 1 to 2, pB represents 0 or 1, and ――――― represents a single bond or a double bond, wherein a sum of mB and pB is an integer less than or equal to 4 (explanation of the groups excerpted a necessary part), has potent leukotriene receptor antagonistic effects, in combination with an excellent oral activity. For describing symbols in the formula, the necessary parts have been excerpted.

However, even though various kinds of substituents are described in the afore-referenced Patent Document, there is no disclosure or suggestion of effects that may be obtained based on the kind of substituents and/or substitution positions. Particularly, Patent Document 2 is completely silent on a scheme to improve the duration of drug efficacy with retaining a potent oral activity. Furthermore, in Patent Document 2, the example compound wherein $V^B$ represents a triple bond was only 4-(1-(carboxymethyl)-7-{[2-hydroxy-4-(4-phenoxybutoxy)phenyl]ethynyl}-1H-indol-3-yl)butanoic acid described in Example 101.

DISCLOSURE OF THE INVENTION

Therefore, there is a demand to find a cysLT$_1$/cysLT$_2$ receptor antagonist having potent oral activity and long-lasting effects.

This and other objects of the present invention have been achieved by the finding that the compound of the formula (I) is useful as a therapeutic drug for respiratory diseases. Namely, the present invention relates to:

(1) A compound of the formula (I):

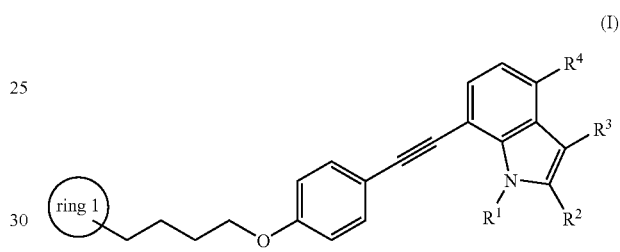

wherein:
$R^1$ represents a carboxymethyl group, or a 3-carboxypropyl group,
$R^2$ represents a hydrogen atom, or a C1-4 alkyl group,
$R^3$ represents a [1-(carboxymethyl)cyclopropyl]methyl group, or a 3-carboxypropyl group,
$R^4$ represents a hydrogen atom, or a halogen atom, and ring 1 represents:

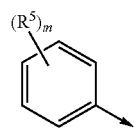

wherein $R^5$ represents a C1-4 alkyl group, or a halogen atom, m represents 0 or an integer of 1 to 5, $R^5$ may be the same or different when m is 2 or greater, and an arrow binds to a butyloxy group; or a salt, solvate or prodrug thereof.

(2) The compound according to the above item (1), wherein ring 1 is

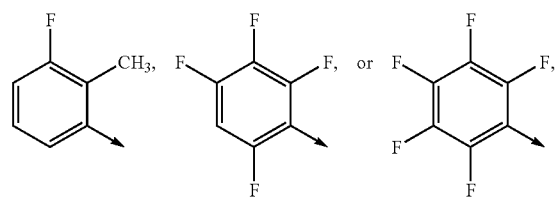

wherein an arrow has the same meanings as in the above item (1).

(3) The compound according to the above item (2), wherein $R^1$ is a 3-carboxypropyl group and $R^3$ is a 3-carboxypropyl group.

(4) The compound according to the above item (1), wherein the compound is (i) 4,4'-[2-methyl-7-({4-[4-(pentafluorophenyl)butoxy]phenyl}ethynyl)-1H-indole-1,3-diyl]dibutanoic acid, (ii) 4,4'-[7-({4-[4-(3-chloro-2-methylphenyl)butoxy]phenyl}ethynyl)-2-methyl-1H-indole-1,3-diyl]dibutanoic acid, (iii) 4,4'-[2-methyl-7-({4-[4-(3,4,5-trifluorophenyl)butoxy]phenyl}ethynyl)-1H-indole-1,3-diyl]dibutanoic acid, (iv) 4,4'-[7-({4-[4-(2,3-difluorophenoxy)butoxy]phenyl}ethynyl)-2-methyl-1H-indole-1,3-diyl]dibutanoic acid, (v) 4,4'-[7-({4-[4-(3-fluoro-2-methylphenyl)butoxy]phenyl}ethynyl)-2-methyl-1H-indole-1,3-diyl]dibutanoic acid, (vi) 4,4'-[2-methyl-7-({4-[4-(2,3,4,5-tetrafluorophenyl)butoxy]phenyl}ethynyl)-1H-indole-1,3-diyl]dibutanoic acid, (vii) 4,4'-[2-methyl-7-({4-[4-(2,3,4,6-tetrafluorophenyl)butoxy]phenyl}ethynyl)-1H-indole-1,3-diyl]dibutanoic acid, (viii) 4,4'-[7-({4-[4-(4-fluoro-2-methylphenyl)butoxy]phenyl}ethynyl)-2-methyl-1H-indole-1,3-diyl]dibutanoic acid, (ix) 4,4'-[7-({4-[4-(4-fluoro-3-methylphenyl)butoxy]phenyl}ethynyl)-2-methyl-1H-indole-1,3-diyl]dibutanoic acid, (x) 4,4'-[4-fluoro-2-methyl-7-({4-[4-(pentafluorophenyl)butoxy]phenyl}ethynyl)-1H-indole-1,3-diyl]dibutanoic acid, (xi) 4,4'-[7-({4-[4-(3-chloro-2-methylphenyl)butoxy]phenyl}ethynyl)-4-fluoro-2-methyl-1H-indole-1,3-diyl]dibutanoic acid, (xii) 4,4'-[4-fluoro-7-({4-[4-(3-fluoro-2-methylphenyl)butoxy]phenyl}ethynyl)-2-methyl-1H-indole-1,3-diyl]dibutanoic acid, (xiii) 4,4'-[4-fluoro-2-methyl-7-({4-[4-(2,3,4,6-tetrafluorophenyl)butoxy]phenyl}ethynyl)-1H-indole-1,3-diyl]dibutanoic acid, (xiv) [3-{[1-(carboxymethyl)cyclopropyl]methyl}-2-methyl-7-({4-[4-(pentafluorophenyl)butoxy]phenyl}ethynyl)-1H-indol-1-yl]acetic acid, (xv) (1-{[1-(carboxymethyl)-7-({4-[4-(3-chloro-2-methylphenyl)butoxy]phenyl}ethynyl)-2-methyl-1H-indol-3-yl]methyl}cyclopropyl)acetic acid, (xvi) [3-{[1-(carboxymethyl)cyclopropyl]methyl}-7-({4-[4-(3-fluoro-2-methylphenyl)butoxy]phenyl}ethynyl)-2-methyl-1H-indol-1-yl]acetic acid, or (xvii) 4,4'-[7-({4-[4-(pentafluorophenyl)butoxy]phenyl}ethynyl)-1H-indole-1,3-diyl]dibutanoic acid.

(5) A pharmaceutical composition containing a compound of the formula (I), or a salt, solvate or prodrug thereof described in the above item (1) as an active ingredient.

(6) The composition according to the above item (5), which is a $cysLT_1/cysLT_2$ receptor antagonist, (7) The composition according to the above item (6), which is an agent for the prevention and/or treatment of a $cysLT_1/cysLT_2$ receptor-mediated disease, (8) The composition according to the above item (7), wherein the $cysLT_1/cysLT_2$ receptor-mediated disease is a respiratory disease, (9) The composition according to the above item (8), wherein the respiratory disease is asthma, chronic obstructive pulmonary disease, pulmonary emphysema, chronic bronchitis, pneumonia, severe acute respiratory syndrome, acute respiratory distress syndrome, allergic rhinitis, sinusitis, pulmonary fibrosis or coughing,

(10) A medicament containing the compound of the formula (I), or a salt, solvate or prodrug thereof described in the above item (1), and one or more members selected from a leukotriene receptor antagonist, a steroidal agent, an antihistamine agent, a phosphodiesterase inhibitor, an elastase inhibitor, an anticholinergic agent, a 5-lipoxygenase inhibitor, prostaglandins, a non-steroidal anti-inflammatory agent, a sympathomimetic agent, a thromboxane synthase inhibitor, and a thromboxane receptor antagonist,

(11) A method for the prevention and/or treatment of the $cysLT_1/cysLT_2$ receptor-mediated disease in a mammal, which comprises administering to the mammal in need thereof an effective amount of the compound of the formula (I), or a salt, solvate or prodrug thereof described in the above item (1), and

(12) Use of the compound of the formula (I), or a salt, solvate or prodrug thereof described in the above item (1), for the manufacture of an agent for the prevention and/or treatment of the $cysLT_1/cysLT_2$ receptor-mediated disease.

DETAILED DESCRIPTION OF THE INVENTION

Figure 1:
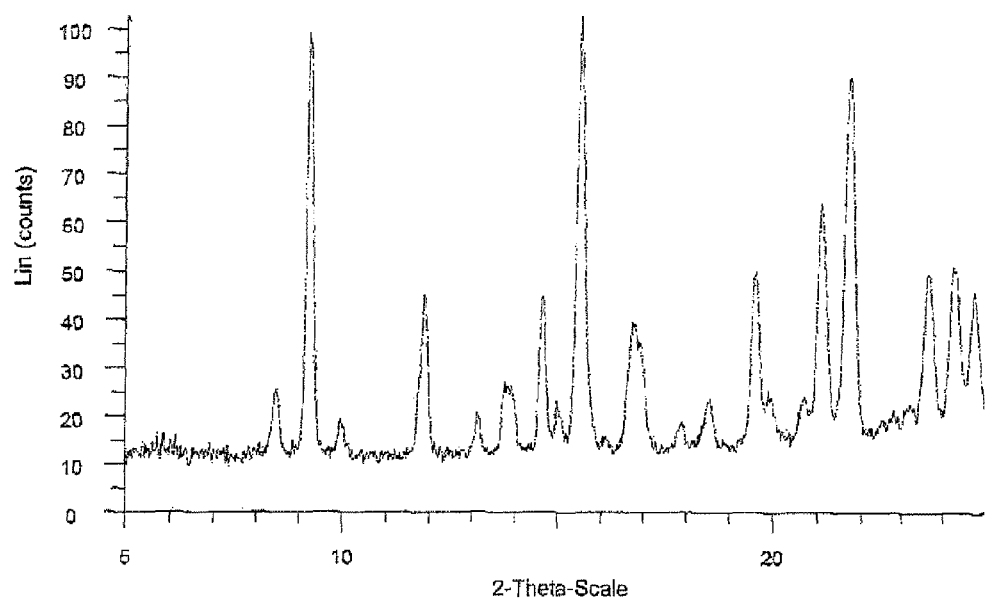
FIG. 1 shows a chart of powdered X-ray diffraction spectrum of a crystal of 4,4'-[2-methyl-7-({4-[4-(pentafluorophenyl)butoxy]phenyl}ethynyl)-1H-indole-1,3-diyl]dibutanoic acid.

As a result of intensive research to solve the above-mentioned problems, the inventors of the present invention found that a compound of the formula (I) strongly antagonizes $cysLT_1/cysLT_2$ receptors and exhibits long-lasting effects even in case of oral administration.

In the present invention, $R^1$ represents a carboxymethyl group, or a 3-carboxypropyl group.

In the present invention, $R^2$ represents a hydrogen atom, or a C1-4 alkyl group. Examples of the C1-4 alkyl group may include methyl, ethyl, n-propyl, isopropyl, n-butyl, isobutyl, sec-butyl, tert-butyl, and the like.

In the present invention, $R^3$ represents a [1-(carboxymethyl)cyclopropyl]methyl group, or a 3-carboxypropyl group.

In the present invention, R⁴ represents a hydrogen atom, or a halogen atom. Examples of the halogen atom may include a fluorine atom, a chlorine atom, a bromine atom, an iodine atom, and the like.

In the present invention, ring 1 represents

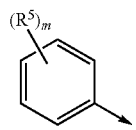

wherein $R^5$ represents a C1-4 alkyl group, or a halogen atom, m represents 0 or an integer of 1 to 5, $R^5$ may be the same or different when m is 2 or greater, and an arrow binds to a butyloxy group. The "C1-4 alkyl group" represented by $R^5$ has the same meaning as the C1-4 alkyl group represented by $R^2$. The halogen atom represented by $R^5$ has the same meaning as the halogen atom represented by $R^4$.

In the present invention, it is preferable that $R^1$ is a 3-carboxypropyl group.

In the present invention, it is preferable that $R^2$ is a C1-4 alkyl group, and more preferably a methyl group.

In the present invention, it is preferable that $R^3$ is a 3-carboxypropyl group.

In the present invention, it is preferable that $R^4$ is a hydrogen atom, or a fluorine atom.

In the present invention, it is preferable that $R^5$ is a methyl group, or a fluorine atom.

In the present invention, it is preferable that m is an integer of 2 to 5.

In the present invention, it is preferable that ring 1 is

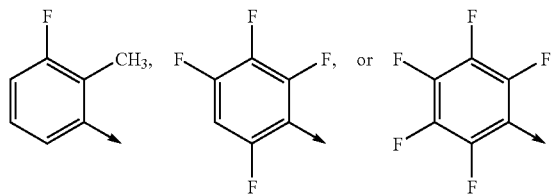

wherein an arrow binds to a butyloxy group.

In the present invention, it is preferable that formula (I) is formula (I-1):

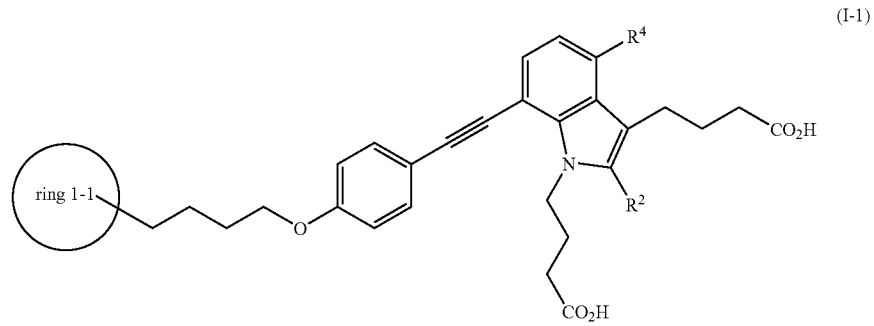

(I-1)

wherein $R^2$ represents a hydrogen atom, or a C1-4 alkyl group, $R^4$ represents a hydrogen atom, or a halogen atom, and ring 1-1 represents:

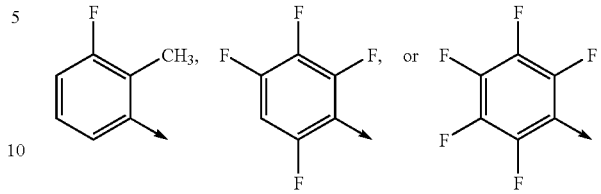

wherein an arrow binds to a butyloxy group.

In the present invention, specific examples of the preferable compound may include:
(1) 4,4'-[2-methyl-7-({4-[4-(pentafluorophenyl)butoxy]phenyl}ethynyl)-1H-indole-1,3-diyl]dibutanoic acid, (2) 4,4'-[7-({4-[4-(3-chloro-2-methylphenyl)butoxy]phenyl}ethynyl)-2-methyl-1H-indole-1,3-diyl]dibutanoic acid, (3) 4,4'-[2-methyl-7-({4-[4-(3,4,5-trifluorophenyl)butoxy]phenyl}ethynyl)-1H-indole-1,3-diyl]dibutanoic acid, (4) 4,4'-[7-({4-[4-(2,3-difluorophenoxy)butoxy]phenyl}ethynyl)-2-methyl-1H-indole-1,3-diyl]dibutanoic acid, (5) 4,4'-[7-({4-[4-(3-fluoro-2-methylphenyl)butoxy]phenyl}ethynyl)-2-methyl-1H-indole-1,3-diyl]dibutanoic acid, (6) 4,4'-[2-methyl-7-({4-[4-(2,3,4,5-tetrafluorophenyl)butoxy]phenyl}ethynyl)-1H-indole-1,3-diyl]dibutanoic acid, (7) 4,4'-[2-methyl-7-({4-[4-(2,3,4,6-tetrafluorophenyl)butoxy]phenyl}ethynyl)-1H-indole-1,3-diyl]dibutanoic acid, (8) 4,4'-[7-({4-[4-(4-fluoro-2-methylphenyl)butoxy]phenyl}ethynyl)-2-methyl-1H-indole-1,3-diyl]dibutanoic acid, (9) 4,4'-[7-({4-[4-(4-fluoro-3-methylphenyl)butoxy]phenyl}ethynyl)-2-methyl-1H-indole-1,3-diyl]dibutanoic acid, (10) 4,4'-[4-fluoro-2-methyl-7-({4-[4-(pentafluorophenyl)butoxy]phenyl}ethynyl)-1H-indole-1,3-diyl]dibutanoic acid, (11) 4,4'-[7-({4-[4-(3-chloro-2-methylphenyl)butoxy]phenyl}ethynyl)-4-fluoro-2-methyl-1H-indole-1,3-diyl]dibutanoic acid, (12) 4,4'-[4-fluoro-7-({4-[4-(3-fluoro-2-methylphenyl)butoxy]phenyl}ethynyl)-2-methyl-1H-indole-1,3-diyl]dibutanoic acid, (13) 4,4'-[4-fluoro-2-methyl-7-({4-[4-(2,3,4,6-tetrafluorophenyl)butoxy]phenyl}ethynyl)-1H-indole-1,3-diyl]dibutanoic acid, (14) [3-{[1-(carboxymethyl)cyclopropyl]methyl}-2-methyl-7-({4-[4-(pentafluorophenyl)butoxy]phenyl}ethynyl)-1H-indol-1-yl]acetic acid, (15) (1-{[1-(carboxymethyl)-7-({4-[4-(3-chloro-2-methylphenyl)butoxy]phenyl}ethynyl)-2-methyl-1H-indol-3-yl]methyl}cyclopropyl)acetic acid, (16) [3-{[1-(carboxymethyl)cyclopropyl]methyl}-7-({4-[4-(3-fluoro-2-methylphenyl)butoxy]phenyl}ethynyl)-2-methyl-1H-indol-1-yl]acetic acid, or (17) 4,4'-[7-({4-[4-(pentafluorophenyl)butoxy]phenyl}ethynyl)-1H-indole-1,3-diyl]dibutanoic acid, and salts, solvates or prodrugs thereof.

More preferable compound is 4,4'-[2-methyl-7-({4-[4-(pentafluorophenyl)butoxy]phenyl}ethynyl)-1H-indole-1,3-diyl]dibutanoic acid, 4,4'-[4-fluoro-7-({4-[4-(3-fluoro-2-methylphenyl)butoxy]phenyl}ethynyl)-2-methyl-1H-indole-1,3-diyl]dibutanoic acid, or 4,4'-[4-fluoro-2-methyl-7-({4-[4-(2,3,4,6-tetrafluorophenyl)butoxy]phenyl}ethynyl)-1H-indole-1,3-diyl]dibutanoic acid, salts, solvates or prodrugs thereof.

The compound of the present invention of the formula (I) may be prepared by known methods, for example, the methods described hereinafter, methods similar to them, or methods described in the Examples. In each following preparation method, starting materials may be used in the form of salts. The below-mentioned pharmaceutically acceptable salts of the formula (I) can be used as the salts.

The compound of the formula (I) may be prepared according to alkaline hydrolysis reaction of a compound of the formula (II):

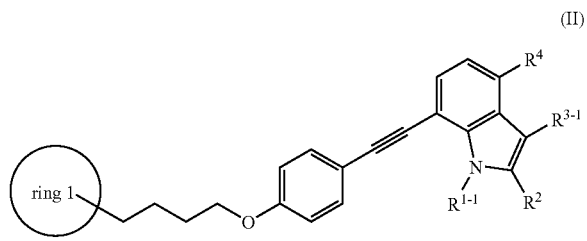

(II)

wherein, $R^{1-1}$ represents a methoxycarbonylmethyl group, a ethoxycarbonylmethyl group, a 3-(methoxycarbonyl)propyl group, or a 3-(ethoxycarbonyl)propyl group, and $R^{3-1}$ represents an [1-(methoxycarbonylmethyl)cyclopropyl]methyl group, an [1-(ethoxycarbonylmethyl)cyclopropyl]methyl group, a 3-(methoxycarbonyl)propyl group, or a 3-(ethoxycarbonyl)propyl group.

The alkaline hydrolysis reaction of the compound of the formula (II) is carried out for example, in an organic solvent (ethylene glycol, methanol, ethanol, tetrahydrofuran, dioxane, dimethoxyethane, etc.), using a hydroxide of alkali metals (sodium hydroxide, potassium hydroxide, lithium hydroxide, etc.), a hydroxide of alkaline earth metals (barium hydroxide, calcium hydroxide, etc.) or a carbonate (sodium carbonate, potassium carbonate, etc.) or an aqueous solution thereof or a mixture thereof at a temperature of 0 to 120° C.

The compound of the formula (II) can be prepared according to the method as shown in Reaction Scheme 1. In the Reaction Scheme 1, X represents a bromine atom, an iodine atom, or a trifluoromethanesulfonyloxy group, AcO represents an acetoxy group, Z represents a halogen atom, a hydroxy group, a methanesulfonyloxy group, or a p-toluenesulfonyloxy group, and other symbols represent the same meaning as defined above.

Reaction Scheme 1

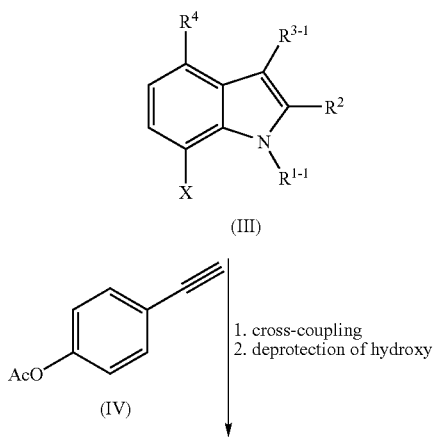

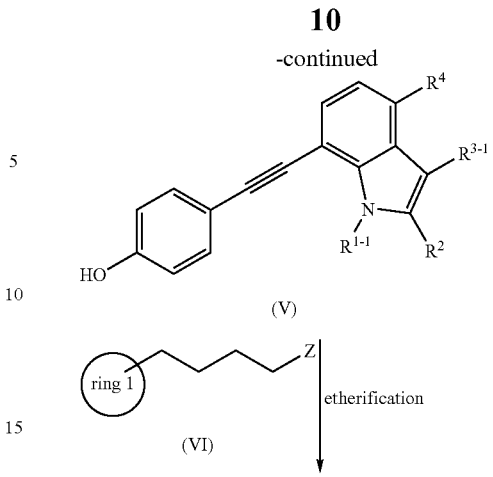

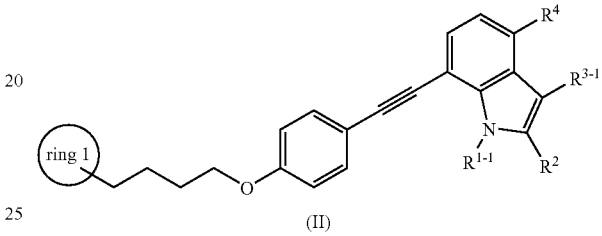

In the Reaction Scheme 1, the cross-coupling reaction, the deprotection reaction of a hydroxy group, and the etherification reaction may be carried out under conditions as set forth below, or under conditions of Examples as described in the present specification.

The cross-coupling reaction between the compound of the formula (III) and the compound of the formula (IV) is carried out, for example, in an organic solvent (ethyl acetate, isopropyl acetate, benzene, toluene, xylene, heptane, cyclohexane, tetrahydrofuran, dioxane, dimethoxyethane, ethanol, isopropanol, polyethylene glycol, dimethylsulfoxide, N,N-dimethylformamide, N,N-dimethylacetamide, N-methyl-2-pyrrolidinone, methylene chloride, chloroform, acetone, acetonitrile, water, a mixture thereof, etc.), in the presence or absence of a base (diethylamine, triethylamine, propylamine, diisopropylamine, diisopropylethylamine, dibutylamine, tributylamine, pyrrolidine, piperidine, N-methylpiperidine, 1,4-diazabicyclo[2.2.2]octane (DABCO), pyridine, sodium hydroxide, sodium hydrogen carbonate, sodium carbonate, potassium carbonate, cesium carbonate, sodium phosphate, potassium phosphate, potassium fluoride, etc.) and a catalyst (palladium catalyst (for example, tetrakis(triphenylphosphine)palladium (Pd(PPh$_3$)$_4$), dichlorobis(triphenylphosphine)palladium (PdCl$_2$(PPh$_3$)$_2$), palladium acetate (Pd(OAc)$_2$), palladium dichloride (PdCl$_2$), palladium black, 1,1'-bis(diphenylphosphinoferrocene)dichloropalladium (PdCl$_2$(dppf)$_2$), dichlorodiallyl palladium (PdCl$_2$(allyl)$_2$), palladium phenylbis(triphenylphosphine) iodide (PhPdI(PPh$_3$)$_2$), tris(dibenzylideneacetone)dipalladium (Pd$_2$(DBA)$_3$), bis(tri-tert-butylphosphine)palladium (Pd($^t$Bu$_3$P)$_2$), etc.) alone, or a mixture thereof with a ligand (for example, triphenylphosphine, tri-tert-butylphosphine, etc.), or a mixture thereof with a copper catalyst (e.g., copper(I) iodide, etc), and in the presence or absence of a phase-transfer catalyst (for example, tetrabutylammonium fluoride, tetrabutylammonium bromide, tetrabutylammonium iodide, tetrabutylammonium acetate, etc.) at from room temperature to 120° C.

Following to the cross-coupling reaction, the deprotection reaction of the hydroxy group is carried out, for example, in an organic solvent (methanol, ethanol, tetrahydrofuran, dioxane, dimethoxyethane or a mixture thereof, etc.), using a hydroxide of alkali metals (sodium hydroxide, potassium hydroxide, lithium hydroxide, etc.), a hydroxide of alkaline earth metals (barium hydroxide, calcium hydroxide, etc.) or a carbonate (sodium carbonate, potassium carbonate, cesium carbonate, etc.) or an aqueous solution thereof or a mixture thereof at a temperature of 0 to 100° C.

(1) When Z is a halogen atom, a methanesulfonyloxy group, or a p-toluenesulfonyloxy group, the etherification between the compound of the formula (V) and the compound of the formula (VI) is carried out, for example, in an organic solvent (such as dimethylformamide, dimethylsulfoxide, N,N-dimethylacetamide, N-methyl-2-pyrrolidinone, 1,3-dimethyl-2-imidazolidinone, chloroform, methylene chloride, diethylether, tetrahydrofuran, benzene, or toluene), in the presence of a hydroxide of alkali metals (such as sodium hydroxide, potassium hydroxide, or lithium hydroxide), a hydroxide of alkaline earth metals (such as barium hydroxide, or calcium hydroxide) or a carbonate (such as sodium carbonate, potassium carbonate, or cesium carbonate), a phosphate of alkali metals (such as potassium phosphate) or an aqueous solution thereof or a mixture thereof, and in the presence or absence of a phase-transfer catalyst (for example, tetrabutylammonium fluoride, tetrabutylammonium bromide, tetrabutylammonium iodide, tetrabutylammonium acetate, etc.) at a temperature of 0° C. to 120° C.

(2) When Z is a hydroxy group, the etherification reaction is carried out, for example, in an organic solvent (such as dichloromethane, diethylether, tetrahydrofuran, acetonitrile, benzene, or toluene), in the presence of an azo compound (such as diethyl azodicarboxylate, diisopropyl azodicarboxylate, 1,1'-(azodicarbonyl)dipiperidine, or 1,1'-azobis(N,N-dimethylformamide)) and a phosphine compound (such as triphenylphosphine, tributylphosphine, or trimethylphosphine), at a temperature of 0 to 60° C.

The indole compound of the formula (III) may be prepared, for example, by using the method described in Example 2, 10, 20, or 51 of the present specification, or a conventional known method.

The compounds which are used as starting materials or reagents and of the formulae (III), (IV) and (VI) are known per se or can be easily prepared by using the methods described in Examples of the present specification, or any conventional known method, for example, methods described in "*Comprehensive Organic Transformations: A Guide to Functional Group Preparations,* 2nd Edition (written by Richard C. Larock, John Wiley & Sons Inc., 1999)".

In each reaction in the present specification, as will be apparent to those skilled in the art, the reaction with heating may be carried out using a water bath, an oil bath, a sand bath, or microwave.

In each reaction in the present specification, a solid phase-supported reagent which is appropriately supported on a polymer (for example, polystyrene, polyacrylamide, polypropylene, polyethylene glycol, etc.) may also be used.

In each reaction in the present specification, the reaction product can be purified by conventional purification means, for example, distillation under normal pressure or reduced pressure, high performance liquid chromatography using a silica gel or magnesium silicate, thin layer chromatography, ion-exchange resin, scavenger resin or column chromatography or washing, or recrystallization. The purification may be carried out for every reaction, or may be carried out after the completion of some reactions.

Unless otherwise specifically mentioned, all isomers are included in the present invention. For example, tautomers, polar compounds (high polar compound and low polar compound) generated by chromatographic separation, equilibrium compounds, rotamers, and mixtures thereof in any proportion are all included in the present invention.

The compound of the formula (I) can be converted into a salt by using the methods described in Examples of the present specification, or any conventional known method. Preferable salts are pharmaceutically acceptable salts.

Examples of the salt of the compound include salts of alkali metals, salts of alkaline earth metals, ammonium salts, and amine salts.

It is preferable that the salt is water-soluble. Examples of a suitable salt include salts of alkali metals (such as potassium and sodium), salts of alkaline earth metals (such as calcium and magnesium), ammonium salts, and salts of pharmaceutically acceptable organic amines (such as tetramethylammonium, triethylamine, methylamine, dimethylamine, cyclopentylamine, benzylamine, phenethylamine, piperidine, monoethanolamine, diethanolamine, tris(hydroxymethyl) aminomethane, lysine, arginine, and N-methyl-D-glucamine).

The compound of the formula (I) and a salt thereof can be converted into solvates by using the methods described in Examples of the present specification, or any conventional known method. It is preferable that the solvate is nontoxic and water-soluble. Examples of an appropriate solvate may include solvates such as hydrate and alcoholate (for example, ethanolate, etc.). The $cysLT_1/cysLT_2$ receptor-antagonizing compound may also be used in the form of a prodrug of the compound of the formula (I).

The term "prodrug" of the compound of the formula (I) refers to a compound which is converted to the compound of the formula (I) by reaction with an enzyme, gastric acid, or the like in the living body. Examples of the prodrug of the compound of the formula (I) include compounds wherein a carboxy group represented by $R^1$ and/or $R^3$ is, for example, esterified or amidated (for example, compounds wherein a carboxy group of the compound of the formula (I) is ethylesterified, isopropylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, 1-{[(cyclohexyloxy)carbonyl]oxy}ethylesterified, methylamidated, etc.), or compounds wherein the carboxyl group is replaced by a hydroxymethyl group, etc. These compounds can be prepared by a method known per se. The prodrug of the compound of the formula (I) may be either of a hydrate and a non-hydrate.

In addition, the compound of the formula (I) may be labeled with an isotope (e.g., $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, etc.) and so on.

[Toxicity]

The compound of the formula (I) has a very low toxicity and is considered to be safe enough for pharmaceutical use.

[Application to Pharmaceuticals]

The compound of the present invention is intended to antagonize the $cysLT_1/cysLT_2$ receptor. Accordingly, the compound is useful as, for example, airway contraction inhibitors, inflammatory cell (for example, eosinophils, neutrophils, lymphocytes, basophils, etc.) infiltration inhibitors, mucus secretion inhibitors, or inhibitors of increased airway hypersensitivity.

Furthermore, the compound of the present invention is useful as an agent for preventing and/or treating for $cysLT_1/cysLT_2$ receptor-associated diseases, for example, respiratory diseases (for example, asthma (bronchial asthma, aspirin-induced asthma, exercise-induced asthma, etc.), chronic obstructive pulmonary diseases (COPD), pulmonary emphysema, chronic bronchitis, pneumonia (interstitial pneumonia, eosinophilic pneumonia, etc.), severe acute respiratory syndrome (SARS), acute respiratory distress syndrome (ARDS), apnea syndrome (sleep apnea syndrome, sleep-disordered breathing accompanied by adenotonsillar hypertrophy, sleep-disordered breathing after adenoidectomy/tonsillectomy, or the like), allergic rhinitis, sinusitis (acute sinusitis, chronic sinusitis, etc.), pulmonary fibrosis, coughing (chronic coughing, etc.), and the like), or as an expectorant agent, or as an antitussive agent.

Furthermore, the compound of the present invention is also useful as an agent for the improvement of respiratory function. As used herein, the term "respiratory function" refers to, for example, inflow or outflow of air into/from the lung (pulmonary vital capacity), delivery of oxygen from the lung to the blood to result in discharge of $CO_2$ from the blood to the outside of the body (oxygen exchange capacity), respiratory resistance, or the like.

As used herein, the term "respiratory organ" refers to a body part which is involved in respiration, such as airway, oral cavity, nasal cavity, nasal sinuses, trachea, bronchi, bronchioli, and lung.

In addition, the compound of the present invention is also useful for preventing and/or treating other diseases in which the $cysLT_1/cysLT_2$ receptor is involved, such as cardiovascular diseases (for example, angina pectoris, myocardial infarction, acute coronary syndromes, cardiac insufficiency, arrhythmia, cardiomyopathy (dilated cardiomyopathy, hypertrophic cardiomyopathy, etc.), pericarditis, valvulitis, myocarditis, cardiac tamponade, low cardiac output syndrome, mitral stenosis, etc.), cystic fibrosis, atherosclerosis, pulmonary fibrosis, cerebral infarction, cerebral edema, aneurysm headache (migraine, cluster headache, tension-type headache, etc.), gynecological diseases (endometriosis, dysmenorrhea, etc.), Meniere's disease, epilepsy, cancer, renal diseases, gastrointestinal ulceration, inflammatory bowel disease, and the like.

As used herein, the term "$cysLT_1/cysLT_2$ receptor antagonistic activity" means that the compound of the present invention exhibits antagonistic effects on both of the $cysLT_1$ receptor and the $cysLT_2$ receptor.

The compound of the present invention may also be administered in combination with other medicaments for the purpose of 1) supplementation and/or enhancement of preventive and/or treatment effects of the compound of the present invention etc., 2) improvement in pharmacokinetics and absorption and reduction of dose of the compound of the present invention etc., and/or 3) reduction of side effects of the compound of the present invention etc.

The compound of the present invention and the other medicaments may be administered in the form of a combination drug having these components formulated into one preparation or may be administered in separate preparations. In the case where these medicaments are administered in separate preparations, they may be administered simultaneously or at different times. In the latter case, the compound of the present invention may be administered before the other medicaments. Alternatively, the other medicaments may be administered before the compound of the present invention. The method for the administration of these may be the same or different.

The above-mentioned other medicaments may be either low-molecular compounds or high-molecular proteins, polypeptides, polynucleotides (DNAs, RNAs, and genes), antisenses, decoys, antibodies, vaccines, etc. The dose of the other medicaments may be appropriately selected taking the clinically used dose as a standard. The formulation ratio between the compound of the present invention and the other medicaments may be appropriately selected, depending on the age and body weight of a subject to be treated, the method and time of administration, the disease to be targeted, its symptoms or conditions, the combination, etc. For example, the other medicaments may be used in a range of 0.01 to 100 parts by mass, relative to 1 part by mass of the compound of the present invention. The other medicaments may be administered alone or in any combination thereof, for example, any one or more compounds selected from the following same or different groups at appropriate ratios. The other medicaments which serve to supplement and/or enhance the preventive and/or treatment effects of the compound of the present invention are understood to encompass not only the ones which have ever been discovered, but also the ones to be discovered in the future, on the basis of the above-mentioned mechanism.

The diseases on which the above-described combination drug is effective in terms of preventive and/or treatment effects are not specifically limited. The diseases may be those in which the preventive and/or treatment effects of the compound of the present invention are supplemented and/or enhanced.

Examples of the other medicaments, which act to supplement and/or enhance the preventive and/or treatment effects of the compound of the present invention against asthma, include leukotriene receptor antagonists, antihistamine agents, phosphodiesterase inhibitors, elastase inhibitors, anticholinergic agents, antiallergic agents (chemical mediator release inhibitors, histamine antagonists, thromboxane synthase inhibitors, thromboxane receptor antagonists, Th2 cytokine inhibitors, etc.), steroidal agents, bronchodilating agents (xanthine derivatives, sympathomimetic agents, parasympatholytic agents), vaccine therapy agents, gold formulations, Chinese herbal medicines, non-steroidal anti-inflammatory agents, 5-lipoxygenase inhibitors, 5-lipoxygenase activating protein antagonists, leukotriene synthesis inhibitors, prostaglandins, cannabinoid-2 receptor stimulants, antitussive agents, expectorant agents, extracts from cutaneous tissue of rabbit inoculated with vaccinia virus, and the like.

Examples of the leukotriene receptor antagonist include pranlukast hydrate, montelukast sodium, zafirlukast, MK-571, LY-203647, WY-46016, WY-48422, WY-49353, WY-49451, RG-12553, MDL-43291, CGP-44044A, RG-14524, LY-287192, LY-290324, L-695499, RPR-105735B, WAY-125007, OT-4003, LM-1376, LY-290154, SR-2566, L-740515, LM-1453, CP-195494, LM-1484, CR-3465, ablukast, pobilukast, sulukast, L-648051, RG-12525, RG-7152, SK&F-106203, SR-2640, WY-50295, iralukast sodium, verlukast, MCC-847, BAY-x-7195, ritolukast, cinalukast, CGP-44826, FK-011, YM-158, MEN-91507, KCA-757, RS-601, RS-635, S-36496, ZD-3523, DS-4574, pirodomast, AS-35, YM-57158, MC1826, NZ-107, 4414-CERM, YM-16638, Wy-48252, Wy-44329, Wy-48090, VUF-4679, tomelukast, SM-11044, SC-39070, OT-3473, N-2401, LY-243364, L-649923, doqualast, DP-1934, YM-17551, Wy-47120, VUF-K-8707, SK&F-88046, SK&F-101132, SK&F-102922, LY-137617, LY-163443, LY-302905, L-647438, L-708738, KY-234, FPL-55712, CP-288886, S-36527, CGP-35949, CS-615, MDL-19301D, SCH-40120, and ZD-3705, etc.

It is preferable that the leukotriene receptor antagonist is pranlukast hydrate, montelukast sodium, zafirlukast or MK-571, and it is more preferable that the leukotriene receptor antagonist is pranlukast hydrate, montelukast sodium or zafirlukast.

Examples of the antihistamine agent include diphenhydramine, diphenylpyraline hydrochloride, diphenylpyraline teoclate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andolast, auranofin, acrivastine, etc.

A phosphodiesterase 4 inhibitor is preferable as the phosphodiesterase inhibitor. Examples of the phosphodiesterase 4 inhibitor include rolipram, cilomilast (trade name: Ariflo®), Bay19-8004, NIK-616, roflumilast (BY-217), cipamfylline (BRL-61063), atizoram (CP-80633), SCH-351591, YM-976, V-11294A, PD-168787, D-4396, IC-485, etc.

Examples of the elastase inhibitor include sivelestat sodium hydrate (ONO-5046), ONO-6818, MR-889, PBI-1101, EPI-HNE-4, R-665, ZD-0892, ZD-8321, GW-311616, AE-3763, DMP-777, L-659286, L-658758, L-680833, L-683845, etc.

Examples of the anticholinergic agent include ipratropium bromide, oxitropium bromide, flutropium bromide, cimetropium bromide, temiverine, tiotropium bromide, revatropate (UK-112166), etc.

Among the antiallergic agents, examples of the chemical mediator release inhibitor include sodium cromoglycate, tranilast, amlexanox, repirinast, ibudilast, pemirolast potassium, tazanolast, nedocromil, cromoglycate, israpafant, etc.

Among the antiallergic agents, examples of the histamine antagonist include ketotifen fumarate, azelastine hydrochloride, oxatomide, mequitazine, terfenadine, emedastine difumarate, epinastine hydrochloride, ebastin, cetirizine hydrochloride, olopatadine hydrochloride, loratadine, fexofenadine, etc.

Among the antiallergic agents, examples of the thromboxane synthase inhibitor include ozagrel hydrochloride, imitrodast sodium, etc.

Among the antiallergic agents, examples of the thromboxane receptor antagonist include seratrodast, ramatroban, domitroban calcium hydrate, KT-2-962, etc.

Among the antiallergic agents, examples of the Th2 cytokine inhibitor include suplatast tosilate, etc.

Steroidal agents as external medicines include clobetasol propionate, diflorasone acetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone dipropionate, triamcinolone acetonide, flumethasone pivalate, alclometasone dipropionate, clobetasone butyrate, prednisolone, fludroxycortide, etc.

Steroidal agents as internal medicines and injections include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyl acetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone, etc. Inhalant medicines include beclometasone dipropionate, fluticasone propionate, budesonide, flunisolide, triamcinolone, ST-126P, ciclesonide, dexamethasone palmitate, mometasone furoate, prasterone sulfonate, deflazacort, methylprednisolone suleptanate, methylprednisolone sodium succinate, etc.

Among the bronchodilating agents, examples of the xanthine derivative include aminophylline, theophylline, doxophylline, cipamfylline, diprophylline, proxyphylline, choline theophylline, etc.

Among the bronchodilating agents, examples of the sympathomimetic agent include epinephrine, ephedrine hydrochloride, dl-methylephedrine hydrochloride, methoxyphenamine hydrochloride, isoproterenol sulfate, isoproterenol hydrochloride, orciprenaline sulfate, clorprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromide, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KUR-1246, KUL-7211, AR-C89855, S-1319, etc.

Among the bronchodilating agents, examples of the parasympatholytic agent include ipratropium bromide, flutropium bromide, oxitropium bromide, cimetropium bromide, temiverine, tiotropium bromide, revatropate (UK-112166), etc.

Examples of the vaccine therapy agent include paspat, asthremedin, broncasma berna, CS-560, etc.

Examples of the gold formulation include sodium aurothiomalate, etc.

Examples of the basic non-steroidal anti-inflammatory agent include tiaramide hydrochloride, tinoridine hydrochloride, epirizole, emorfazone, etc.

Examples of the 5-lipoxygenase inhibitor include Zileuton (Zyflo®), docebenone, piripost, SCH-40120, WY-50295, E-6700, ML-3000, TMK-688, ZD-2138, darbufelone mesylate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175, ETH-615, AM-103, MK-0633, etc.

Examples of the 5-lipoxygenase activating protein antagonist include MK-591, MK-886, MK-0633, AM-103, etc.

Examples of the leukotriene synthase inhibitor include auranofin, proglumetacin maleate, L-674636, A-81834, UPA-780, A-93178, MK-886, REV-5901A, SCH-40120, MK-591, Bay-x-1005, Bay-y-1015, DTI-0026, amlexanox, E-6700, etc.

Examples of the prostaglandins (hereinafter referred to briefly as "PG") include PG receptor agonists, PG receptor antagonists, etc.

Examples of the PG receptor include PGE receptors (EP1, EP2, EP3, EP4), PGD receptors (DP, CRTH2), PGF receptor (FP), PGI receptor (IP), TX receptor (TP), etc.

Examples of the antitussive agent include codeine phosphate, dihydrocodeine phosphate, oxymetebanol, dextromethorphan hydrobromide, pentoxyverine citrate, dimemorfan phosphate, oxeladin citrate, chloperastine, benproperine phosphate, clofedanol hydrochloride, fominoben hydrochloride, noscapine, tipepidine hibenzate, eprazinone hydrochloride, plantago herb extract, etc.

Examples of the expectorant agent include foeniculated ammonia spirit, sodium hydrogen carbonate, potassium iodide, bromhexine hydrochloride, cherry bark extract, carbocysteine, fudosteine, ambroxol hydrochloride, controlled release preparation of ambroxol hydrochloride, methylcysteine hydrochloride, acetylcysteine, L-ethylcysteine hydrochloride, tyloxapol, etc.

The above-mentioned other agents are preferably leukotriene receptor antagonists, steroidal agents or sympathomimetic agents.

The dosage form, which is aimed at conducting the present invention into practice, may be in the form of either a pharmaceutical preparation containing the $cysLT_1/cysLT_2$ receptor antagonist compound and other medicaments for supplementation and/or enhancement of the treatment effects of the compound formulated in one dosage form, or a pharmaceutical preparation containing each of the ingredients processed individually into separate dosage forms. Such processing into the dosage forms may be carried out in accordance with the known method.

For the above-mentioned purposes, a pharmaceutical composition containing the compound of the present invention or a combination drug of the compound of the present invention with other agents is administered typically systemically or topically, orally or parenterally.

The dosage may vary depending on age, body weight, symptom, treatment effect, administration route, duration of the treatment and the like. Generally, for an adult, from 1 mg to 1,000 mg per dose is orally administered once to several times a day (preferably, once a day), or from 0.1 mg to 100 mg per dose is parenterally (preferably, intravenously) administered once to several times a day, or continuously administered into a vein for from 1 to 24 hours a day.

As the dosage may fluctuate according to various conditions as described above, a dose lower than the above-specified dose may in some instances be adequate, whereas a dose in excess of the dose range may in some cases be required.

The compound is administered in the form of solid formulations for oral administration or liquid formulations for oral administration, or injectable formulations, external medicines, suppositories, eye drops, inhalants and the like for parenteral administration, for the purpose of the present invention.

The solid formulations for oral administration include, for example, tablets, pills, capsules, powders, and granules. Capsules include hard capsules and soft capsules.

In such solid formulations for oral administration, one or more active agent(s) are directly formulated according to usual methods, or mixed with one or more of an excipient (lactose, mannitol, glucose, microcrystalline cellulose, starch, etc.), a binding agent (hydroxypropyl cellulose, polyvinylpyrrolidone, magnesium aluminometasilicate, etc.), a disintegrating agent (calcium cellulose glycolate, etc.), a lubricant (magnesium stearate, etc.), a stabilizing agent or a solubilizing agent (glutamic acid, aspartic acid, etc.), and the like. If necessary, the formulations may be coated with a coating agent (such as sugar, gelatin, hydroxypropyl cellulose, or hydroxypropylmethyl cellulose phthalate), or may be coated with two or more layers. Included are also capsules made of absorbable materials such as gelatin.

The liquid formulations for oral administration include pharmaceutically acceptable aqueous solutions, suspensions, emulsions, syrups, elixirs, etc. In such liquid formulations, one or more of the active agent(s) are dissolved, suspended or emulsified in a commonly used diluent (e.g., purified water, ethanol, or a mixture thereof). Furthermore, such liquid formulations may also include wetting agents, suspending agents, emulsifying agents, sweetening agents, flavoring agents, aromatic agents, preservatives, or buffering agents.

The injectable formulations for parenteral administration include, for example, solutions, suspensions, emulsions, and solid formulations for injection which are dissolved, suspended or emulsified into solvent(s) for injection before use. The injectable formulation is prepared by dissolving, suspending or emulsifying one or more active substances in a solvent. Examples of the solvent may include distilled water for injection, saline, vegetable oil, propylene glycol, polyethylene glycol or alcohols such as ethanol, and any combination thereof. The injectable formulation may further contain a stabilizing agent, a solubilizing agent (glutamic acid, aspartic acid, polysorbate 80 (registered trademark), etc.), a suspending agent, an emulsifying agent, a soothing agent, a buffer or a preservative, etc. These are prepared by sterilizing in the final process or by a sterile operation method. Alternatively, they may be used by firstly producing sterile solid formulations such as freeze-dried formulations and dissolving them in sterilized or sterile distilled water for injection or another sterile solvent prior to their use.

The eye drops for parenteral administration may be in the form of liquid eye drops, suspension-type eye drops, emulsion-type eye drops or eye drops which are dissolved in a solvent upon actual use, or eye ointments.

These eye drops are prepared by known methods. For example, in the case of liquid eye drops, they may be prepared by appropriately selecting and incorporating a tonicity agent (sodium chloride, concentrated glycerin, etc.), a buffer (sodium phosphate, sodium acetate, etc.), a surface active agent (Polysorbate 80, polyoxyl 40 stearate, polyoxyethylene-hardened castor oil, etc.), a stabilizing agent (sodium citrate, sodium edetate, etc.), and an antiseptic (benzalkonium chloride, Paraben, etc.), and the like, depending on the needs. These are prepared by sterilizing in the final process or by a sterile operation method.

The inhalable formulation for parenteral administration may be in the form of an aerosol, inhalable liquid formulation or inhalable powder. The inhalable liquid formulation may be dissolved, suspended or emulsified in water or other appropriate medium prior to application.

These inhalable formulations may be prepared according to known methods. For example, inhalable liquid formulations may be prepared by appropriately selecting an antiseptic (benzalkonium chloride, Paraben, etc.), a coloring agent, a buffer (sodium phosphate, sodium acetate, etc.), a tonicity agent (sodium chloride, concentrated glycerin, etc.), a thickening agent (carboxyvinyl polymer, etc.), an absorption promoter, and the like, depending on the needs.

Inhalable powders may be prepared by appropriately selecting and incorporating a lubricant (stearic acid, a salt thereof (e.g. magnesium stearate), etc.), a binding agent (starch, dextrin, etc.), an excipient (lactose, cellulose, etc.), a coloring agent, an antiseptic agent (benzalkonium chloride, Paraben, etc.), an absorption promoter, and the like, depending on the needs.

Inhalable liquid formulations may typically be administered by sprayers (e.g. atomizer, nebulizer, etc.) and inhalable powders may be administered by using inhalers for powder formulations.

Other formulations for parenteral administration include liquid preparations for external application, ointments, liniments, spray formulations, suppositories, pessaries for intravaginal administration, and the like, which contain one or more active substances and may be processed by conventional methods.

The spray formulation includes, besides commonly used diluents, a stabilizing agent such as sodium hydrogen sulfite, and a tonicity-imparting buffer, e.g. a tonicity agent such as sodium chloride, sodium citrate, or citric acid. For the preparation of the spray formulation, details thereof can be found, for example, in U.S. Pat. Nos. 2,868,691 and 3,095,355.

EXAMPLES

Although the present invention will be described in more detail by the following Examples and Biological Examples, it is not limited thereto.

The parenthesized solvents as indicated in the position of chromatographic separation and TLC denote the elution solvents or developing solvents as used, with the ratio being on a volume basis. The parenthesized solvent as indicated under the heading of NMR denotes the solvent used in the measurement.

Compounds in the following Examples were named using ACD/Name (version 6.00, manufactured by Advanced Chemistry Development Inc.).

In the powdered X-ray diffraction spectrum in confirming the identity of crystals, the diffraction angle (2θ) and their overall patterns are important, and the relative intensity is somewhat variable depending on direction of crystal growth, size of particle, and the condition of measurement. Further, in differential scanning calorimetry (DSC) in confirming the identity of crystals, the overall patterns are important but somewhat variable depending on the condition of measurement.

Example 1

Ethyl 4-(7-bromo-2-methyl-1H-indol-3-yl)butanoate

To a solution of (2-bromophenyl)hydrazine hydrochloride (14 g) in ethanol (60 mL), 5-acetylvaleric acid (9.0 g) was added. The reaction mixture was stirred at 50° C. for 40 minutes, and concentrated sulfuric acid (6.0 mL) was added thereto, followed by heating under reflux for 16 hours. The reaction mixture was added to a saturated aqueous sodium hydrogen carbonate solution which was then extracted with ethyl acetate and dried over anhydrous sodium sulfate, followed by concentratration under reduced pressure. The resulting residue was purified by column chromatography (hexane:ethyl acetate=8:1) to obtain the title compound (15 g) having the following physical properties.

TLC:Rf 0.54 (hexane:ethyl acetate=3:1)

$^1$H-NMR (CDCl$_3$): δ 1.23, 1.89-2.00, 2.31, 2.39, 2.72, 4.10, 6.95, 7.24, 7.43, 7.91

Example 2

Diethyl 4,4'-(7-bromo-2-methyl-1H-indole-1,3-diyl)dibutanoate

The compound (18 g) prepared in Example 1 was dissolved in dimethylsulfoxide (110 mL), and ethyl 4-bromobutyrate (76 g) and cesium carbonate (145 g) were added thereto. The reaction mixture was stirred at 50° C. for 16 hours. Water was added to the reaction mixture which was then extracted with ethyl acetate. The organic layer was dried over magnesium sulfate, and concentrated under reduced pressure. The resulting residue was purified by a medium-pressure preparative liquid chromatograph W-prep 2XY (manufactured by Yamazen Corporation, column: main column 4 L, inject column 3 L; hexane:ethyl acetate=9:1→4:1) to obtain the title compound (24 g) having the following physical properties.

TLC:Rf 0.31 (hexane:acetone=17:3)

$^1$H-NMR (CDCl$_3$): δ 1.24, 1.26, 1.83-1.98, 1.98-2.12, 2.30, 2.36, 2.39, 2.73, 4.09-4.20, 4.47-4.52, 6.88, 7.26, 7.42

Example 3

Diethyl 4,4'-(7-{[4-(acetyloxy)phenyl]ethynyl}-2-methyl-1H-indole-1,3-diyl)dibutanoate To a solution of the compound (5.5 g) prepared in Example 2 and 4-ethynylphenyl acetate (3.8 g) in acetonitrile (25 mL), diisopropylamine (3.3 mL) and bis(tri-tert-butylphosphine)palladium (320 mg) were added under an argon atmosphere, followed by stirring at room temperature for 15 hours. The reaction mixture was filtered through "Celite" (registered trademark), and the filtrate was concentrated. The resulting residue was purified by a medium-pressure preparative liquid chromatograph W-prep 2XY (manufactured by Yamazen Corporation, column: main column 3L, inject column 2L; hexane:ethyl acetate=9:1→7:3) to obtain the title compound (5.9 g) having the following physical properties.

TLC:Rf 0.26 (hexane:ethyl acetate=3:1)

$^1$H-NMR (CDCl$_3$): δ 1.21, 1.24, 1.86-1.98, 2.10-2.22, 2.25-2.37, 2.75, 4.04-4.14, 4.59-4.65, 7.03, 7.11, 7.32, 7.50, 7.55

Example 4

Diethyl 4,4'-{7-[(4-hydroxyphenyl)ethynyl]-2-methyl-1H-indole-1,3-diyl}dibutanoate Potassium carbonate (3.1 g) was added to a solution of the compound (5.9 g) prepared in Example 3 in ethanol (11 mL) and dimethoxyethane (11 mL), followed by stirring at room temperature for 15 hours. The reaction mixture was diluted with water, and extracted with ethyl acetate. The organic layer was washed sequentially with water and brine, dried over magnesium sulfate, followed by concentration under reduced pressure. The resulting residue was purified by a medium-pressure preparative liquid chromatograph W-prep 2XY (manufactured by Yamazen Corporation, column: main column 2L, inject column L; hexane:ethyl acetate=9:1→6:4) to obtain the title compound (4.8 g) having the following physical properties.

TLC:Rf 0.29 (hexane:ethyl acetate=2:1)

$^1$H-NMR (CDCl$_3$): δ 1.22, 1.26, 1.82-1.99, 2.05-2.21, 2.32, 2.36, 2.75, 4.04-4.14, 4.62, 5.39, 6.83, 7.01, 7.30, 7.42, 7.48

Example 5

4-(pentafluorophenyl)buta-3-in-1-ol

To a solution of 1-bromo-2,3,4,5,6-pentafluorobenzene (50 g) in triethylamine (200 mL), 3-butyn-1-ol (15 g), triphenylphosphine (2.7 g), dichlorobistriphenylphosphinepalladium (3.6 g) and copper (I) iodide (1.9 g) were added, followed by stirring at 80° C. for 16 hours. The reaction mixture was cooled to room temperature, and tert-butyl methyl ether (500 mL) was added thereto, followed by stirring at 0° C. for 30 minutes. The reaction mixture was filtered through "Celite" (registered trademark), and the filtrate was concentrated. The resulting residue was purified by flash column chromatography (hexane:ethyl acetate=95:5→65:35) to give the title compound (43 g) having the following physical properties.

TLC:Rf 0.28 (hexane:ethyl acetate=4:1)

$^1$H-NMR (CDCl$_3$): δ 1.81, 2.78, 3.86

Example 6

4-(pentafluorophenyl)butan-1-ol

To a solution of the compound (43 g) prepared in Example 5 in ethanol (430 mL), 10% palladium carbon (50% water content, 4.3 g) was added. The atmosphere inside the reaction system was replaced with argon, followed by stirring at room temperature under a hydrogen atmosphere for 6 hours. Thereto, 10% palladium carbon (50% water content, 4.3 g) was added, followed by stirring at room temperature under a hydrogen atmosphere for 2 hours. The reaction mixture was filtered through "Celite" (registered trademark), and the filtrate was concentrated to obtain the title compound (41 g) having the following physical properties.

TLC:Rf 0.31 (hexane:ethyl acetate=4:1)
$^1$H-NMR (CDCl$_3$): δ 1.20-1.38, 1.52-1.76, 2.74, 3.68

Example 7

4-(pentafluorophenyl)butyl 4-methylbenzene sulfonate

Triethylamine (46 mL) was added to a solution of the compound (40 g) prepared in Example 6 in toluene (330 mL), followed by stirring at 0° C. p-toluenesulfonyl chloride (41 g) and trimethylamine hydrochloride (1.6 g) were added thereto, followed by stirring at 0° C. for 2 hours, and at room temperature for another 20 hours. The reaction mixture was cooled to 0° C., and N,N-dimethylethane-1,2-diamine (7.3 g) was added thereto, followed by stirring for 15 minutes. Water was added to the reaction mixture, and the aqueous layer was made acidic by addition of 2N hydrochloric acid, followed by separation of the organic layer. The aqueous layer was extracted with toluene; the combined organic layer was washed sequentially with water and brine; and dried over anhydrous magnesium sulfate and filtered, followed by evaporation of the solvent under reduced pressure. The solid components were washed with hexane-ethyl acetate (10:1) to obtain the title compound (52 g) having the following physical properties.

TLC:Rf 0.48 (hexane:ethyl acetate=5:1)
$^1$H-NMR (CDCl$_3$): δ 1.55-1.77, 2.45, 2.66, 4.05, 7.35, 7.78

Example 8

Diethyl 4,4'-[2-methyl-7-({4-[4-(pentafluorophenyl)butoxy]phenyl}ethynyl)-1H-indole-1,3-diyl]dibutanoate Cesium carbonate (220 mg) was added to solution of the compound (180 mg) prepared in Example 4 and the compound (150 mg) prepared in Example 7 in N,N-dimethylformamide (1.0 mL), followed by stirring at room temperature for 10 hours. The reaction mixture was diluted with water, and extracted with ethyl acetate. The organic layer was washed sequentially with water and brine and dried over magnesium sulfate, followed by concentration under reduced pressure. The resulting residue was purified by a medium-pressure preparative liquid chromatograph W-prep 2XY (manufactured by Yamazen Corporation, column: main column M, inject column S; hexane:ethyl acetate=9:1→8:2) to obtain the title compound (160 mg) having the following physical properties.

TLC:Rf 0.52 (hexane:ethyl acetate=3:1)
$^1$H-NMR (CDCl$_3$): δ 1.19-1.26, 1.71-2.00, 2.05-2.10, 2.25-2.40, 2.68-2.85, 3.99-4.18, 4.62, 6.87, 7.01, 7.31, 7.42-7.52

Example 9

4,4'-[2-methyl-7-({4-[4-(pentafluorophenyl)butoxy]phenyl}ethynyl)-1H-indole-1,3-diyl]dibutanoic Acid

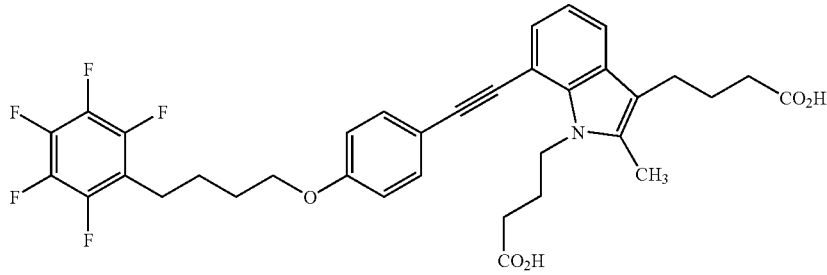

A 2N aqueous sodium hydroxide solution (1.0 mL) was added to a solution of the compound (150 mg) prepared in Example 8 in dimethoxyethane (2.0 mL) and ethanol (2.0 mL), followed by stirring at room temperature for 4 hours. Ice-cold 2N hydrochloric acid (1.0 mL) was added under ice-cooling to the reaction mixture, followed by extraction with ethyl acetate. The organic layer was washed sequentially with water and brine and dried over magnesium sulfate, followed by concentration under reduced pressure. The resulting residue was washed with diisopropylether-hexane (9:1), and dried under reduced pressure to obtain the title compound (120 mg) having the following physical properties.

TLC:Rf 0.40 (methylene chloride:methanol=9:1)
$^1$H-NMR (DMSO-D$_6$): δ 1.63-1.82, 1.87-2.02, 2.14-2.24, 2.33, 2.67, 2.76, 4.03, 4.54, 6.94-7.03, 7.22, 7.44-7.54, 12.08

Examples 9 (1) to (8)

By the same procedure as in Example 8→Example 9 using the corresponding sulfonate instead of the compound prepared in Example 7, the compounds of the present invention having the following physical properties were obtained.

Example 9 (1)

4,4'-[7-({4-[4-(3-chloro-2-methylphenyl)butoxy]phenyl}ethynyl)-2-methyl-1H-indole-1,3-diyl]dibutanoic Acid TLC:Rf 0.36 (methylene chloride:methanol=9:1)
$^1$H-NMR (DMSO-D$_6$): δ 1.59-1.87, 1.88-2.03, 2.12-2.23, 2.31, 2.33, 2.61-2.77, 4.05, 4.54, 6.93-7.03, 7.07-7.18, 7.19-7.29, 7.42-7.58, 12.05

Example 9 (2)

4,4'-[2-methyl-7-({4-[4-(3,4,5-trifluorophenyl)bu-toxy]phenyl}ethynyl)-1H-indole-1,3-diyl]dibutanoic acid TLC:Rf 0.18 (methylene chloride:methanol=9:1)
$^1$H-NMR (DMSO-D$_6$): δ 1.65-1.80, 1.88-2.02, 2.14-2.24, 2.34, 2.60-2.74, 4.02, 4.54, 6.83-7.02, 7.14-7.25, 7.42-7.52, 12.04

Example 9 (3)

4,4'-[7-({4-[4-(2,3-difluorophenoxy)butoxy]phenyl}ethynyl)-2-methyl-1H-indole-1,3-diyl]dibutanoic acid TLC:Rf 0.37 (methylene chloride:methanol=9:1)
$^1$H-NMR (DMSO-D$_6$): δ 1.66-1.81, 1.83-2.02, 2.13-2.24, 2.34, 2.62-2.74, 4.05-4.12, 4.13-4.20, 4.49-4.60, 6.91-7.06, 7.07-7.18, 7.22, 7.44-7.56, 12.08

Example 9 (4)

4,4'-[7-({4-[4-(3-fluoro-2-methylphenyl)butoxy]phenyl}ethynyl)-2-methyl-1H-indole-1,3-diyl]dibutanoic acid TLC:Rf 0.42 (methylene chloride:methanol=9:1)
$^1$H-NMR (DMSO-D$_6$): δ 1.55-1.86, 1.86-2.04, 2.11-2.25, 2.34, 2.67, 4.05, 4.54, 6.90-7.07, 7.08-7.19, 7.22, 7.40-7.57, 12.09

Example 9 (5)

4,4'-[2-methyl-7-({4-[4-(2,3,4,5-tetrafluorophenyl)butoxy]phenyl}ethynyl)-1H-indole-1,3-diyl]dibutanoic acid TLC:Rf 0.35 (methylene chloride:methanol=9:1)
$^1$H-NMR (DMSO-D$_6$): δ 1.64-1.81, 1.87-2.04, 2.13-2.24, 2.33, 2.62-2.76, 4.03, 4.49-4.60, 6.92-7.03, 7.22, 7.33-7.54, 12.08

Example 9 (6)

4,4'-[2-methyl-7-({4-[4-(2,3,4,6-tetrafluorophenyl)butoxy]phenyl}ethynyl)-1H-indole-1,3-diyl]dibutanoic Acid TLC:Rf 0.43 (methylene chloride:methanol=9:1)
$^1$H-NMR (DMSO-D$_6$): δ 1.61-1.84, 1.86-2.02, 2.14-2.25, 2.33, 2.62-2.77, 4.03, 4.46-4.60, 6.92-7.03, 7.22, 7.39-7.55, 12.08

Example 9 (7)

4,4'-[7-({4-[4-(4-fluoro-2-methylphenyl)butoxy]phenyl}ethynyl)-2-methyl-1H-indole-1,3-diyl]dibutanoic Acid TLC:Rf 0.33 (methylene chloride:methanol=9:1)
$^1$H-NMR (DMSO-D$_6$): δ 1.52-1.85, 1.87-2.05, 2.12-2.24, 2.26, 2.33, 2.60, 2.67, 4.04, 4.54, 6.83-7.05, 7.09-7.28, 7.39-7.56, 12.09

Example 9 (8)

4,4'-[7-({4-[4-(4-fluoro-3-methylphenyl)butoxy]phenyl}ethynyl)-2-methyl-1H-indole-1,3-diyl]dibutanoic acid TLC:Rf 0.35 (methylene chloride:methanol=9:1)
$^1$H-NMR (DMSO-D$_6$): δ 1.59-1.84, 1.87-2.05, 2.17, 2.18-2.24, 2.33, 2.67, 4.05, 4.54, 6.92-7.05, 7.08-7.18, 7.22, 7.44-7.56, 12.09

Example 10

Ethyl 4-[7-bromo-1-(2-ethoxy-2-oxoethyl)-2-methyl-1H-indol-3-yl]butanoate

By the same procedure as in Example 2 using ethyl bromoacetate instead of ethyl 4-bromobutyrate, the title compound having the following physical properties was obtained.
TLC:Rf 0.52 (hexane:ethyl acetate=3:1)
$^1$H-NMR (CDCl$_3$): δ 1.24, 1.27, 1.85-1.99, 2.27, 2.30, 2.75, 4.11, 4.24, 5.28, 6.92, 7.26, 7.44

Example 11

4-[1-(carboxymethyl)-2-methyl-7-({4-[4-(2,3,4,5-tetrafluorophenyl)butoxy]phenyl}ethynyl)-1H-indol-3-yl]butanoic Acid By the same procedure as in Example 3→Example 4→Example 8→Example 9 using the compound prepared in Example 10 instead of the compound prepared in Example 2, and using the corresponding sulfonate instead of the compound prepared in Example 7, the compound of the present invention having the following physical properties was obtained.
TLC:Rf 0.25 (methylene chloride:methanol=9:1)
$^1$H-NMR (DMSO-D$_6$): δ 1.66-1.81, 2.16-2.24, 2.25, 2.62-2.76, 3.99-4.08, 5.38, 6.94-7.03, 7.19, 7.32-7.45, 7.45-7.53, 12.02, 12.96

Example 12

Ethyl 4-(7-bromo-1-{[1-(2-ethoxy-2-oxoethyl)cyclopropyl]methyl}-2-methyl-1H-indol-3-yl)butanoate To a solution of the compound (2.0 g) prepared in Example 1 in dimethylsulfoxide (12 mL), [1-(bromomethyl)cyclopropyl]acetonitrile (1.6 g) and cesium carbonate (3.0 g) were added, and the reaction mixture was stirred at room temperature for 5 hours. Cesium carbonate (3.0 g) was added thereto, followed by stirring overnight. Furthermore, cesium carbonate (3.0 g) was added again, followed by stirring for 9 hours. [1-(bromomethyl)cyclopropyl]acetonitrile (1.6 g) and cesium carbonate (2.0 g) were added thereto, followed by further stirring overnight. Water was added to the reaction mixture and neutralized by addition of an aqueous hydrochloric acid solution, followed by extraction with ethyl acetate. The organic layer was washed with water and brine and dried over anhydrous sodium sulfate, followed by concentration under reduced pressure. The resulting residue was purified by silica gel column chromatography (hexane:ethyl acetate=95:5→75:25)) to give an N-alkyl compound (1.3 g).

To solution of the N-alkyl compound (1.7 g) in ethanol (7.0 mL) and ethylene glycol (3.5 mL), 12 N aqueous sodium hydroxide solution (3.4 mL) was added, followed by heating at 100° C. for 11 hours, and at 120° C. for 5 hours. Under ice-cooling, the reaction mixture was adjusted to an acidic pH by addition of 5N hydrochloric acid, followed by extraction with ethyl acetate. The organic layer was washed sequentially with water and brine and dried over magnesium sulfate, followed by concentration under reduced pressure to obtain dicarboxylic acid (1.3 g).

Potassium carbonate (1.1 g) and iodoethane (2.2 g) were added to a solution of dicarboxylic acid (1.3 g) in dimethylformamide (8.0 mL) under an argon atmosphere, followed by stirring at room temperature for 17 hours. The reaction mixture was diluted with water, and extracted with ethyl acetate. The organic layer was washed sequentially with water and brine; dried over magnesium sulfate; and filtered, followed by concentration under reduced pressure. The resulting residue was purified by silica gel column chromatography (hexane:ethyl acetate=95:5→80:20) to obtain the title compound (1.5 g) having the following physical properties.
TLC:Rf 0.49 (hexane:ethyl acetate=4:1)
$^1$H-NMR (CDCl$_3$): δ 0.16-0.29, 0.30-0.47, 1.18-1.34, 1.79-1.96, 2.28, 2.35, 2.42, 2.71, 4.04-4.21, 4.89, 6.85, 7.21-7.28, 7.39

Example 13

4-[1-{[1-(carboxymethyl)cyclopropyl]methyl}-2-methyl-7-({4-[4-(pentafluorophenyl)butoxy]phenyl}ethynyl)-1H-indol-3-yl]butanoic Acid

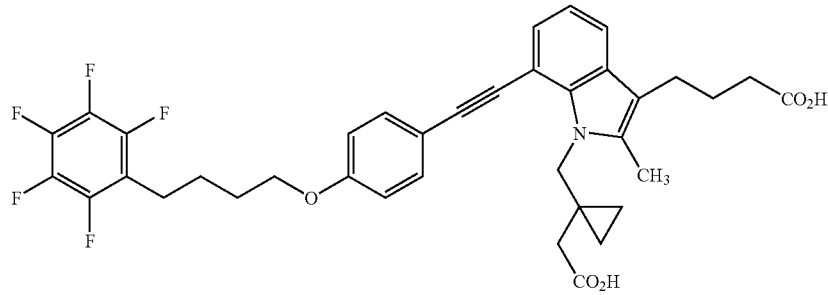

By the same procedure as in Example 3→Example 4→Example 8→Example 9 using the compound prepared in Example 12 instead of the compound prepared in Example 2, the title compound having the following physical properties was obtained.

TLC:Rf 0.43 (methylene chloride:methanol=9:1)
$^1$H-NMR (DMSO-D$_6$): δ 0.05-0.26, 0.27-0.48, 1.61-1.87, 2.18, 2.31, 2.34, 2.66, 2.77, 4.03, 4.90, 6.88-7.04, 7.19, 7.46, 7.51, 12.09

Examples 13 (1) to (6)

By the same procedure as in Example 3→Example 4→Example 8→Example 9 using the compound prepared in Example 12 instead of the compound prepared in Example 2, and using the corresponding sulfonate instead of the compound prepared in Example 7, the compounds of the present invention having the following physical properties were obtained.

Example 13 (1)

4-[1-{[1-(carboxymethyl)cyclopropyl]methyl}-7-({4-[4-(3-chloro-2-methylphenyl)butoxy]phenyl}ethynyl)-2-methyl-1H-indol-3-yl]butanoic Acid TLC:Rf 0.43 (methylene chloride:methanol=9:1)
$^1$H-NMR (DMSO-D$_6$): δ 0.06-0.24, 0.28-0.45, 1.56-1.86, 2.18, 2.29-2.33, 2.34, 2.59-2.78, 4.05, 4.90, 6.89-7.03, 7.06-7.22, 7.25, 7.46, 7.52, 12.09

Example 13 (2)

4-[1-{[1-(carboxymethyl)cyclopropyl]methyl}-2-methyl-7-({4-[4-(3,4,5-trifluorophenyl)butoxy]phenyl}ethynyl)-1H-indol-3-yl]butanoic Acid TLC:Rf 0.40 (methylene chloride:methanol=9:1)
$^1$H-NMR (DMSO-D$_6$): δ 0.12-0.19, 0.34-0.42, 1.66-1.79, 2.18, 2.31, 2.34, 2.60-2.70, 3.99-4.05, 4.90, 6.91-7.02, 7.15-7.25, 7.46, 7.49-7.54, 12.08

Example 13 (3)

4-[1-{[1-(carboxymethyl)cyclopropyl]methyl}-7-({4-[4-(3-fluoro-2-methylphenyl)butoxy]phenyl}ethynyl)-2-methyl-1H-indol-3-yl]butanoic Acid TLC:Rf 0.43 (methylene chloride:methanol=9:1)
$^1$H-NMR (DMSO-D$_6$): δ 0.06-0.25, 0.28-0.47, 1.57-1.88, 2.12-2.23, 2.31, 2.34, 2.59-2.78, 4.05, 4.90, 6.88-7.05, 7.08-7.17, 7.19, 7.46, 7.52, 12.09

Example 13 (4)

4-[1-{[1-(carboxymethyl)cyclopropyl]methyl}-7-({4-[4-(4-fluoro-2-methylphenyl)butoxy]phenyl}ethynyl)-2-methyl-1H-indol-3-yl]butanoic Acid TLC:Rf 0.44 (methylene chloride:methanol=9:1)
$^1$H-NMR (DMSO-D$_6$): δ 0.06-0.24, 0.28-0.45, 1.56-1.85, 2.18, 2.26, 2.31, 2.34, 2.56-2.71, 4.05, 4.90, 6.86-7.06, 7.12-7.24, 7.47, 7.52, 12.11

Example 13 (5)

4-[1-{[1-(carboxymethyl)cyclopropyl]methyl}-2-methyl-7-({4-[4-(2,3,4,6-tetrafluorophenyl)butoxy]phenyl}ethynyl)-1H-indol-3-yl]butanoic Acid TLC:Rf 0.44 (methylene chloride:methanol=9:1)
$^1$H-NMR (DMSO-D$_6$): δ 0.05-0.26, 0.27-0.47, 1.59-1.85, 2.18, 2.31, 2.34, 2.59-2.77, 4.03, 4.90, 6.89-7.04, 7.19, 7.37-7.58, 12.09

Example 13 (6)

4-[1-{[1-(carboxymethyl)cyclopropyl]methyl}-2-methyl-7-({4-[4-(2,3,6-trifluorophenyl)butoxy]phenyl}ethynyl)-1H-indol-3-yl]butanoic Acid TLC:Rf 0.44 (methylene chloride:methanol=9:1)
$^1$H-NMR (DMSO-D$_6$): δ 0.04-0.25, 0.28-0.47, 1.60-1.86, 2.18, 2.31, 2.34, 2.66, 2.73, 4.03, 4.90, 6.89-7.03, 7.04-7.15, 7.19, 7.28-7.42, 7.46, 7.51, 12.09

Example 14

4,4'-[4-fluoro-2-methyl-7-({4-[4-(pentafluorophenyl)butoxy]phenyl}ethynyl)-1H-indole-1,3-diyl]dibutanoic Acid

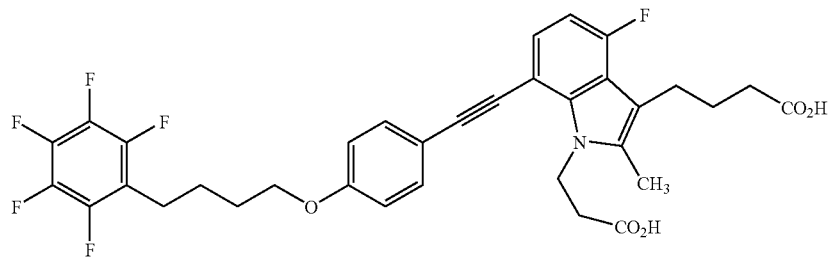

By the same procedure as in Example 1→Example 2→Example 3→Example 4→Example 8→Example 9 using (2-bromo-5-fluorophenyl)hydrazine (which was prepared according to the following procedure: 2-bromo-5-fluoroaniline (20 g) was poured into 5N hydrochloric acid (200 mL) under ice-cooling, followed by stirring for 20 minutes, and a solution of sodium nitrite (8.0 g) in water (20 mL) was slowly added thereto, followed by stirring for 40 minutes. The reaction mixture and a 5N aqueous sodium hydroxide solution (150 mL) were added under ice-cooling to an aqueous solution (200 mL) of sodium sulfite (33 g) and sodium dihydrogen phosphate (1.7 g) with maintaining a pH of 6 or higher, followed by stirring at 75° C. for 1 hour. The reaction mixture was cooled to room temperature and filtered, and the filtrate was concentrated under reduced pressure. The resulting residue was poured into concentrated hydrochloric acid at 60° C., followed by stirring for 2 hours, and at room temperature overnight. The reaction mixture was neutralized under ice-cooling with an aqueous 12N sodium hydroxide solution. The precipitated solid was filtered; washed with water; and dissolved in ethyl acetate. The organic layer was dried over magnesium sulfate, and concentrated under reduced pressure to obtain a hydrazine compound.) instead of (2-bromophenyl)hydrazine hydrochloride, the compound of the present invention having the following physical properties was obtained.

TLC:Rf 0.43 (methylene chloride:methanol=9:1)
$^1$H-NMR (DMSO-D$_6$): δ 1.64-1.84, 1.88-2.02, 2.14-2.23, 2.33, 2.68-2.82, 4.02, 4.49-4.59, 6.76, 6.97, 7.19, 7.47, 12.08

Examples 14 (1) to (3)

By the same procedure as in Example 1→Example 2→Example 3→Example 4→Example 8→Example 9 using the (2-bromo-5-fluorophenyl)hydrazine instead of (2-bromophenyl)hydrazine hydrochloride, and using the corresponding sulfonate instead of the compound prepared in Example 7, the compounds of the present invention having the following physical properties were obtained.

Example 14 (1)

4,4'-[7-({4-[4-(3-chloro-2-methylphenyl)butoxy]phenyl}ethynyl)-4-fluoro-2-methyl-1H-indole-1,3-diyl]dibutanoic Acid TLC:Rf 0.35 (methylene chloride:methanol=9:1)
$^1$H-NMR (DMSO-D$_6$): δ 1.57-1.84, 1.86-2.03, 2.12-2.23, 2.30, 2.32, 2.65-2.79, 4.05, 4.55, 6.76, 6.99, 7.07-7.30, 7.48, 12.08

Example 14 (2)

4,4'-[4-fluoro-7-({4-[4-(3-fluoro-2-methylphenyl)butoxy]phenyl}ethynyl)-2-methyl-1H-indole-1,3-diyl]dibutanoic Acid TLC:Rf 0.58 (methylene chloride:methanol=9:1)
$^1$H-NMR (DMSO-D$_6$): δ 1.59-1.85, 1.87-2.05, 2.10-2.26, 2.32, 2.59-2.82, 4.05, 4.48-4.63, 6.76, 6.91-7.06, 7.08-7.16, 7.20, 7.48, 12.08

Example 14 (3)

4,4'-[4-fluoro-2-methyl-7-({4-[4-(2,3,4,6-tetrafluorophenyl)butoxy]phenyl}ethynyl)-1H-indole-1,3-diyl]dibutanoic Acid TLC:Rf 0.57 (methylene chloride:methanol=9:1)
$^1$H-NMR (DMSO-D$_6$): δ 1.61-1.83, 1.87-2.02, 2.13-2.23, 2.32, 2.64-2.79, 4.02, 4.49-4.61, 6.76, 6.97, 7.20, 7.38-7.58, 12.08

Example 15

4-[1-(carboxymethyl)-4-fluoro-2-methyl-7-({4-[4-(pentafluorophenyl)butoxy]phenyl}ethynyl)-1H-indol-3-yl]butanoic Acid By the same procedure as in Example 1→Example 2→Example 3→Example 4→Example 8→Example 9 using the (2-bromo-5-fluorophenyl)hydrazine instead of (2-bromophenyl)hydrazine hydrochloride, and using ethyl bromoacetate instead of ethyl 4-bromobutyrate, the compound of the present invention having the following physical properties was obtained.

TLC:Rf 0.38 (methylene chloride:methanol=9:1)
$^1$H-NMR (DMSO-D$_6$): δ 1.62-1.84, 2.18, 2.24, 2.66-2.83, 4.03, 5.40, 6.78, 6.97, 7.18, 7.48, 12.02, 13.07

Example 15 (1)

4-[1-(carboxymethyl)-7-({4-[4-(3-chloro-2-methylphenyl)butoxy]phenyl}ethynyl)-4-fluoro-2-methyl-1H-indol-3-yl]butanoic Acid By the same procedure as in Example 1→Example 2→Example 3→Example 4→Example 8→Example 9 using the (2-bromo-5-fluorophenyl)hydrazine instead of (2-bromophenyl)hydrazine hydrochloride; using ethyl bromoacetate instead of ethyl 4-bromobutyrate; and using the corresponding sulfonate instead of the compound prepared in Example 7, the compound of the present invention having the following physical properties was obtained.

TLC:Rf 0.30 (methylene chloride:methanol=9:1)
$^1$H-NMR (DMSO-D$_6$): δ 1.57-1.85, 2.19, 2.24, 2.31, 2.65-2.80, 4.04, 5.40, 6.78, 6.98, 7.08-7.22, 7.26, 7.48, 12.05, 13.10

Example 16

4-[1-{[1-(carboxymethyl)cyclopropyl]methyl}-4-fluoro-2-methyl-7-({4-[4-(pentafluorophenyl)butoxy]phenyl}ethynyl)-1H-indol-3-yl]butanoic Acid

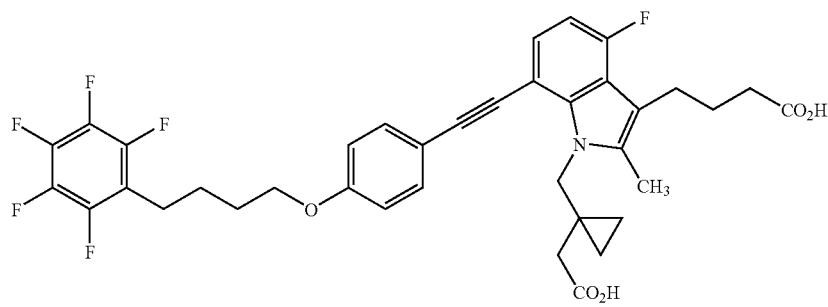

By the same procedure as in Example 1→Example 12→Example 3→Example 4→Example 8→Example 9 using the (2-bromo-5-fluorophenyl)hydrazine instead of (2-bromophenyl)hydrazine hydrochloride, the compound of the present invention having the following physical properties was obtained.

TLC:Rf 0.38 (methylene chloride:methanol=9:1)
$^1$H-NMR (DMSO-D$_6$): δ 0.10-0.21, 0.35-0.44, 1.64-1.84, 2.11-2.21, 2.29-2.32, 2.33, 2.65-2.83, 4.03, 4.91, 6.74, 6.98, 7.18, 7.51, 12.09

Examples 16 (1) to (3)

By the same procedure as in Example 1→Example 12→Example 3→Example 4→Example 8→Example 9 using the (2-bromo-5-fluorophenyl)hydrazine instead of (2-bromophenyl)hydrazine hydrochloride, and using the corresponding sulfonate instead of the compound prepared in Example 7, the compounds of the present invention having the following physical properties were obtained.

Example 16 (1)

4-[1-{[1-(carboxymethyl)cyclopropyl]methyl}-7-({4-[4-(3-chloro-2-methylphenyl)butoxy]phenyl}ethynyl)-4-fluoro-2-methyl-1H-indol-3-yl]butanoic Acid TLC:Rf 0.35 (methylene chloride:methanol=9:1)
$^1$H-NMR (DMSO-D$_6$): δ 0.11-0.20, 0.36-0.44, 1.60-1.86, 2.12-2.21, 2.31, 2.33, 2.66-2.77, 4.02-4.10, 4.91, 6.73, 6.99, 7.07-7.21, 7.25, 7.46-7.55, 12.08

Example 16 (2)

4-[1-{[1-(carboxymethyl)cyclopropyl]methyl}-4-fluoro-2-methyl-7-({4-[4-(2,3,5,6-tetrafluorophenyl)butoxy]phenyl}ethynyl)-1H-indol-3-yl]butanoic Acid TLC:Rf 0.38 (methylene chloride:methanol=9:1)
$^1$H-NMR (DMSO-D$_6$): δ 0.07-0.22, 0.29-0.46, 1.61-1.86, 2.16, 2.31, 2.33, 2.71, 2.79, 4.04, 4.91, 6.74, 6.99, 7.18, 7.51, 7.74, 12.09

Example 16 (3)

4-[1-{[1-(carboxymethyl)cyclopropyl]methyl}-4-fluoro-2-methyl-7-({4-[4-(2,3,4,5-tetrafluorophenyl)butoxy]phenyl}ethynyl)-1H-indol-3-yl]butanoic Acid TLC:Rf 0.30 (methylene chloride:methanol=9:1)
$^1$H-NMR (DMSO-D$_6$): δ 0.12-0.19, 0.35-0.45, 1.64-1.82, 2.16, 2.31, 2.33, 2.63-2.78, 4.03, 4.91, 6.74, 6.95-7.03, 7.18, 7.33-7.45, 7.47-7.58, 12.09

Example 17

{1-[(7-bromo-2-methyl-1H-indol-3-yl)methyl]cyclopropyl}acetonitrile

Ethyl magnesium bromide (3.0M diethyl ether solution, 72 mL) was slowly added dropwise under an argon atmosphere and ice-cooling to a solution of [1-(bromomethyl)cyclopropyl]acetonitrile (15 g) and 7-bromo-2-methyl-1H-indole (45 g) in toluene (250 mL), followed by stirring at 100° C. for 80 minutes. The reaction mixture was cooled to room temperature; quenched with a saturated aqueous ammonium chloride solution, diluted with water; and extracted with ethyl acetate. The organic layer was washed sequentially with water and brine. The organic layer was dried over sodium sulfate, and concentrated under reduced pressure. The resulting residue was purified by a purification system CombiFlash CompanionXL (manufactured by Isco, Co., Ltd., column: RediSep 350 g; hexane:ethyl acetate=95:5->70:30) to obtain title compound (14 g) having the following physical properties.

TLC:Rf 0.64 (hexane:ethyl acetate=2:1)
$^1$H-NMR (CDCl$_3$): δ 0.53-0.60, 0.60-0.68, 2.27, 2.46, 2.89, 6.97, 7.27, 7.47, 8.03

Example 18

{1-[(7-bromo-2-methyl-1H-indol-3-yl)methyl]cyclopropyl}acetic Acid

A solution of sodium hydroxide (28 g) in water (100 mL) was added to a solution of the compound (14 g) prepared in Example 17 in ethanol (100 mL) and ethylene glycol (50 mL), followed by stirring at 100° C. for 1.5 days. The reaction mixture was neutralized under ice-cooling with 5N hydrochloric acid, and extracted with ethyl acetate. The organic layer was washed with brine, dried over magnesium sulfate, and concentrated under reduced pressure to obtain the title compound (19 g) having the following physical properties.

TLC:Rf 0.68 (hexane:ethyl acetate=1:2)

$^1$H-NMR (DMSO-D$_6$): δ 0.28-0.40, 2.11, 2.31, 2.80, 6.86, 7.16, 7.42, 10.90, 12.00

Example 19

Ethyl {1-[(7-bromo-2-methyl-1H-indol-3-yl)methyl]cyclopropyl}acetate

To a solution of the compound (19 g) prepared in Example 18 in N,N-dimethylformamide (100 mL), potassium carbonate (16 g) and ethyl iodide (11 g) were added, followed by stirring at room temperature for 3 hours. The reaction mixture was diluted with water, and extracted with ethyl acetate. The organic layer was washed sequentially with water and brine, dried over magnesium sulfate, and then concentrated under reduced pressure. The resulting residue was purified by a purification system CombiFlash CompanionXL (manufactured by Isco, Co., Ltd., column: RediSep 80 g; hexane:ethyl acetate=80:20) to obtain the title compound (16 g) having the following physical properties.

TLC:Rf 0.58 (hexane:ethyl acetate=4:1)

$^1$H-NMR (CDCl$_3$): δ 0.38-0.50, 1.25, 2.23, 2.40, 2.95, 4.11, 6.93, 7.22, 7.46, 7.98

Example 20

Ethyl (7-bromo-3-{[1-(2-ethoxy-2-oxoethyl)cyclopropyl]methyl}-2-methyl-1H-indol-1-yl)acetate To a solution of the compound (16 g) prepared in Example 19 in N,N-dimethylformamide (100 mL), cesium carbonate (38 g) and ethyl bromoacetate (12 g) were added, followed by stirring at room temperature for 15 hours. Additionally, cesium carbonate (6.0 g) and ethyl bromoacetate (1.5 g) were further added thereto, followed by stirring at room temperature for 4.5 hours and at 50° C. for another 2 hours. The reaction mixture was diluted with water, and extracted with ethyl acetate. The organic layer was washed sequentially with water and brine, dried over magnesium sulfate, and concentrated under reduced pressure. The resulting residue was purified by a purification system CombiFlash CompanionXL (manufactured by Isco, Co., Ltd., column: RediSep 120 g; hexane:ethyl acetate=100:0→80:20) to obtain the title compound (18 g) having the following physical properties.

TLC:Rf 0.42 (hexane:ethyl acetate=4:1)

$^1$H-NMR (CDCl$_3$): δ 0.33-0.41, 1.26, 1.27, 2.27, 2.28, 2.97, 4.15, 4.23, 5.29, 6.90, 7.23, 7.48

Example 21

[3-{[1-(carboxymethyl)cyclopropyl]methyl}-2-methyl-7-({4-[4-(pentafluorophenyl)butoxy]phenyl}ethynyl)-1H-indol-1-yl]acetic Acid By the same procedure as in Example 3→Example 4→Example 8→Example 9 using the compound prepared in Example 20 instead of the compound prepared in Example 2, the compound of the present invention having the following physical properties was obtained.

TLC:Rf 0.46 (methylene chloride:methanol=9:1)

$^1$H-NMR (DMSO-D$_6$): δ 0.31, 1.55-1.89, 2.16, 2.25, 2.76, 2.88, 4.03, 5.39, 6.83-7.06, 7.19, 7.41-7.60, 12.13, 12.86

Examples 21 (1) to (2)

By the same procedure as in Example 3→Example 4→Example 8→Example 9 using the compound prepared in Example 20 instead of the compound prepared in Example 2, and using the corresponding sulfonate instead of the compound prepared in Example 7, the compounds of the present invention having the following physical properties were obtained.

Example 21 (1)

(1-{[1-(carboxymethyl)-7-({4-[4-(3-chloro-2-methylphenyl)butoxy]phenyl}ethynyl)-2-methyl-1H-indol-3-yl]methyl}cyclopropyl)acetic Acid TLC:Rf 0.43 (methylene chloride:methanol=9:1)

$^1$H-NMR (DMSO-D$_6$): δ 0.31, 1.58-1.72, 1.72-1.85, 2.17, 2.25, 2.31, 2.70, 2.89, 4.05, 5.39, 6.92-7.06, 7.07-7.29, 7.41-7.56, 12.19, 12.81

Example 21 (2)

[3-{[1-(carboxymethyl)cyclopropyl]methyl}-7-({4-[4-(3-fluoro-2-methylphenyl)butoxy]phenyl}ethynyl)-2-methyl-1H-indol-1-yl]acetic Acid TLC:Rf 0.43 (methylene chloride:methanol=9:1)

$^1$H-NMR (DMSO-D$_6$): δ 0.31, 1.61-1.72, 1.73-1.84, 2.17, 2.25, 2.67, 2.88, 4.04, 5.39, 6.89-7.03, 7.11, 7.15-7.23, 7.43-7.57, 12.05, 12.79

Example 22

Ethyl 4-(7-bromo-1H-indol-3-yl)-4-oxobutanoate 7-bromo-1H-indole (18 g) was dissolved in methylene chloride (50 mL), and aluminum (III) chloride (6.8 g) and ethyl succinyl chloride (8.4 g) were added thereto under ice-cooling. The reaction mixture was stirred at room temperature for 5 hours. Ice-cold water was added to the reaction mixture which was then extracted with ethyl acetate. The organic layer was washed sequentially with water and brine and dried over magnesium sulfate, followed by concentration under reduced pressure. The resulting residue was washed with diisopropylether, and dried under reduced pressure to obtain the title compound (6.0 g) having the following physical properties.

TLC:Rf 0.53 (hexane:ethyl acetate=1:1)

$^1$H-NMR (CDCl$_3$): δ 1.27, 2.79, 3.23, 4.16, 7.17, 7.44, 7.97, 8.32, 8.72

Example 23

Ethyl 4-(7-bromo-1H-indol-3-yl)butanoate

Sodium borohydride (760 mg) and boron trifluoride-diethyl ether complex (5.8 mL) were added under ice-cooling to a solution of the compound (5.0 g) prepared in Example 22 in tetrahydrofuran (150 mL), followed by stirring at 0° C. for 2 hours. A saturated aqueous ammonium chloride solution was added to the reaction mixture, followed by ethyl acetate extraction. The organic layer was washed sequentially with water and brine and dried over magnesium sulfate, followed by concentration under reduced pressure. The resulting residue was purified by a medium-pressure preparative liquid chromatograph W-prep 2XY (manufactured by Yamazen Corporation, column: main column 2L, inject column L; hexane:ethyl acetate=90:10-85:15) to obtain the title compound (2.9 g) having the following physical properties.

TLC:Rf 0.53 (hexane:ethyl acetate=2:1)

$^1$H-NMR (CDCl$_3$): δ 1.24, 1.98-2.08, 2.36, 2.79, 4.12, 6.99, 7.06, 7.34, 7.55, 8.14

Example 24

Diethyl 4,4'-(7-bromo-1H-indole-1,3-diyl)dibutanoate

The compound (4.4 g) prepared in Example 23 was dissolved in dimethylsulfoxide (14 mL), and ethyl 4-bromobutyrate (5.5 g) and cesium carbonate (9.2 g) were added. The reaction mixture was stirred at 50° C. for 14 hours. Water was added to the reaction mixture, followed by extraction with a mixed solvent (1:1) of hexane and ethyl acetate. The organic layer was washed sequentially with water and brine and dried over magnesium sulfate, followed by concentration under reduced pressure. The resulting residue was purified by a medium-pressure preparative liquid chromatograph W-prep 2XY (manufactured by Yamazen Corporation, column: main column L, inject column L; hexane:ethyl acetate=95:5→85:15) to obtain the title compound (5.9 g) having the following physical properties.

TLC:Rf 0.31 (hexane:acetone=17:3)

$^1$H-NMR (CDCl$_3$): δ 1.22-1.27, 1.91-2.05, 2.08-2.12, 2.27-2.38, 2.74, 4.08-4.16, 4.52, 6.85, 6.91, 7.33, 7.51

Example 25

4,4'-[7-({4-[4-(pentafluorophenyl)butoxy]phenyl}ethynyl)-1H-indole-1,3-diyl]dibutanoic Acid

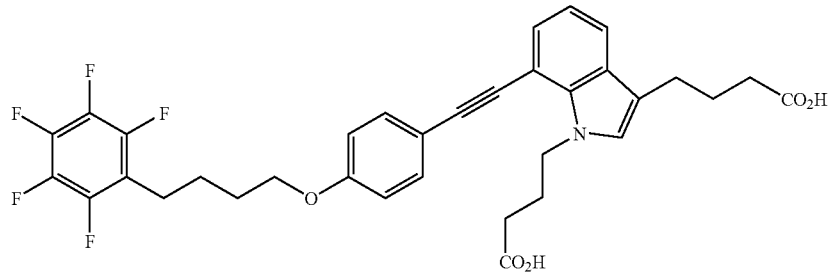

By the same procedure as in Example 3→Example 4→Example 8→Example 9 using the compound prepared in Example 24 instead of the compound prepared in Example 2, the compound of the present invention having the following physical properties was obtained.

TLC:Rf 0.48 (methylene chloride:methanol=9:1)

$^1$H-NMR (DMSO-D$_6$): δ 1.62-1.92, 1.99-2.19, 2.26, 2.68, 2.76, 4.03, 4.56-4.62, 6.93-7.05, 7.16, 7.29, 7.49, 7.57, 12.07

Example 26

4-bromo-1-(phenylsulfonyl)-1H-indole

Under a nitrogen atmosphere, a solution of 4-bromo-1H-indole (200 g) in tetrahydrofuran (2.0 L) was ice-cooled to 0° C., and sodium hydride (49 g) was added thereto, followed by stirring under ice-cooling for 1 hour. Benzenesulfonyl chloride (200 g) was added dropwise under ice-cooling to the reaction mixture, and the ice bath was removed, followed by stirring at room temperature. A saturated aqueous ammonium chloride solution was added to the reaction mixture, followed by ethyl acetate extraction. The organic layer was washed with brine and dried over magnesium sulfate, followed by filteration. The resulting residue was washed with isopropylether-hexane (1:1, 1.0 L), and then dried to obtain the title compound (310 g) having the following physical properties.

TLC:Rf 0.68 (hexane:ethyl acetate=3:1)

$^1$H-NMR (CDCl$_3$): δ 6.74, 7.18, 7.36-7.51, 7.52-7.60, 7.63, 7.84-7.92, 7.92-8.00

Example 27

4-bromo-2-methyl-1-(phenylsulfonyl)-1H-indole n-butyl lithium (1.6M hexane solution, 420 mL) was added under a nitrogen atmosphere to tetrahydrofuran (100 mL), followed by cooling to 10° C. Diisopropylamine (68 g) was added dropwise thereto, and the ice bath was removed, followed by stirring at room temperature for 30 minutes. The reaction mixture was cooled to −60° C. in a dry ice-methanol bath. A solution of the compound (150 g) prepared in Example 26 in tetrahydrofuran (1.0 L) was added dropwise thereto over about 1 hour, and the temperature was warmed to 0° C. The reaction mixture was cooled to −60° C. in a dry ice-methanol bath to which iodomethane (95 g) was then added dropwise over about 20 minutes, followed by warming to 10° C. After the completion of the reaction was confirmed by TLC, a saturated aqueous ammonium chloride solution (500 mL) was added dropwise thereto, followed by further addition of water (500 mL) and twice extraction with ethyl acetate (1.0 L). The organic layer was washed with 1N hydrochloric acid (1.0 L) and brine (500 mL) and dried over magnesium sulfate, followed by filteration. The resulting residue was washed with methanol (500 mL) and dried to obtain the title compound (140 g) having the following physical properties.

TLC:Rf 0.48 (hexane:ethyl acetate=6:1)

$^1$H-NMR (CDCl$_3$): δ 2.61, 6.39-6.48, 7.07-7.17, 7.36, 7.39-7.48, 7.50-7.59, 7.72-7.81, 8.07-8.15

Example 28

4-bromo-2-methyl-1H-indole

To solution of the compound (12 g) prepared in Example 27 in ethanol (35 mL), 5N aqueous sodium hydroxide solution (35 mL) and dimethoxyethane (11 mL) were added under an argon atmosphere, followed by heating under reflux for 6 hours. The reaction mixture was concentrated under reduced pressure, and the resulting residue was cooled to 10° C. Thereafter, the reaction mixture was adjusted to a pH 5 by addition of 5N hydrochloric acid, followed by extraction with ethyl acetate twice. The organic layer was washed sequentially with a saturated aqueous sodium hydrogen carbonate solution, water and brine, and dried over magnesium sulfate. After filtration and concentration under reduced pressure, the resulting residue was purified by silica gel column chromatography (hexane:ethyl acetate=95:5→85:15) to obtain the title compound (7.3 g) having the following physical properties.

TLC:Rf 0.37 (hexane:ethyl acetate=6:1)
$^1$H-NMR (CDCl$_3$): δ 2.41-2.49, 6.24-6.31, 6.90-7.00, 7.18-7.24, 7.99

Example 29

1-(4-bromo-2-methyl-1H-indol-3-yl)-N,N-dimethylmethanamine

The compound (140 g) prepared in Example 28 and N,N-dimethylmethylene ammonium chloride (68 g) were added under a nitrogen atmosphere to N,N-dimethylformamide (1.4 L), followed by stirring at room temperature for 1 hour. The reaction mixture was added to a 5N ice-cooled aqueous sodium hydroxide solution (800 mL), and water (2.0 L) was added thereto, followed by extraction with ethyl acetate twice (2.0 L). The organic layer was washed with water (1.0 L) twice and brine (1.0 L) and dried over magnesium sulfate, followed by concentration under reduced pressure. The resulting residue was washed with hexane (500 mL) and then dried to obtain the title compound (140 g) having the following physical properties.

TLC:Rf 0.23 (butanol:acetic acid:water=3:1:1)
$^1$H-NMR (CDCl$_3$): δ 2.30, 2.31, 3.71, 6.87, 7.10-7.26, 7.20

Example 30

(4-bromo-2-methyl-1H-indol-3-yl)acetonitrile

Dimethyl sulfate (71 g) was added under a nitrogen atmosphere to tetrahydrofuran (1.0 L), followed by cooling to 5° C. or less. Solution of the compound (140 g) prepared in Example 29 in tetrahydrofuran (500 mL) was added dropwise over 1 hour, followed by stirring at 10° C. for 1 hour. The reaction solvent was evaporated under reduced pressure. The resulting residue was dissolved by adding water (1.5 L) and N,N-dimethylformamide (600 mL), followed by adding potassium cyanide (50 g) and stirring at 80° C. for 2 hours. The reaction mixture was cooled to 20° C., and extracted with ethyl acetate (1.0 L) three times. The organic layer was washed with water (1.0 L) three times and brine (1.0 L), and dried over magnesium sulfate. After filtration and concentration under reduced pressure, the resulting residue was washed with isopropylether (200 mL), and then dried to obtain the title compound (100 g) having the following physical properties.

TLC:Rf 0.20 (hexane:ethyl acetate=3:1)
$^1$H-NMR (CDCl$_3$): δ 2.45, 4.11, 6.94-7.02, 7.22-7.24, 7.25-7.29, 8.10

Example 31

(4-bromo-2-methyl-1H-indol-3-yl)acetic Acid

To a solution of the compound (20 g) prepared in Example 30 in ethanol (130 mL), dimethoxyethane (70 mL) and ethylene glycol (70 mL), 12N aqueous sodium hydroxide solution (67 mL) was added, followed by heating under reflux for 32 hours. Under ice-cooling, 5N hydrochloric acid (160 mL) was added to the reaction mixture, followed by ethyl acetate extraction. The organic layer was washed sequentially with water and brine and dried over magnesium sulfate, followed by concentration under reduced pressure. After filtration and concentration under reduced pressure, the resulting residue was washed with hexane, and dried under reduced pressure to obtain the title compound (22 g) having the following physical properties.

TLC:Rf 0.46 (hexane:ethyl acetate=1:4)
$^1$H-NMR (DMSO-D$_6$): δ 2.27, 3.80, 6.87, 7.70, 7.25, 11.19, 12.06

Example 32

Ethyl (4-bromo-2-methyl-1H-indol-3-yl)acetate

To solution of the compound (22 g) prepared in Example 31 in N,N-dimethylformamide (80 mL), potassium carbonate (22 g) and iodoethane (19 g) were added, followed by stirring at room temperature for 15 hours. Water was added under ice-cooling to the reaction mixture, followed by ethyl acetate extraction. The organic layer was washed sequentially with water and brine and dried over magnesium sulfate, followed by concentration under reduced pressure. After filtration and concentration under reduced pressure, the resulting residue was washed with hexane, and dried under reduced pressure to obtain the title compound (22 g) having the following physical properties.

TLC:Rf 0.43 (hexane:ethyl acetate=2:1)
$^1$H-NMR (CDCl$_3$): δ 1.28, 2.26, 3.48, 3.96, 4.20, 6.89, 7.13, 7.19, 8.10

Example 33

Ethyl (4-bromo-1-{[1-(cyanomethyl)cyclopropyl]methyl}-2-methyl-1H-indol-3-yl)acetate The compound (10 g) prepared in Example 32 was dissolved in dimethylsulfoxide (40 mL). Thereto, [1-(bromomethyl)cyclopropyl]acetonitrile (13 g) and cesium carbonate (99 g) were added, and the reaction mixture was stirred at 40° C. for 25 hours. Water was added to the reaction mixture, followed by ethyl acetate extraction. The organic layer was dried over magnesium sulfate, and concentrated under reduced pressure. The resulting residue was washed with diisopropylether and hexane, and dried under reduced pressure to obtain the title compound (11 g) having the following physical properties.

TLC:Rf 0.32 (hexane:ethyl acetate=2:1)
$^1$H-NMR (CDCl$_3$): δ 0.58-0.70, 1.26, 2.29, 2.38, 4.02, 4.17, 4.25, 6.97, 7.22, 7.27

Example 34

(4-bromo-1-{[1-(carboxymethyl)cyclopropyl]methyl}-2-methyl-1H-indol-3-yl)acetic Acid To a solution of the compound (12 g) prepared in Example 33 in ethanol (80 mL), dimethoxyethane (40 mL) and ethylene glycol (40 mL), 12N aqueous sodium hydroxide solution (38 mL) was added, followed by heating under reflux for 29 hours. Under ice-cooling, 5N hydrochloric acid (95 mL) was added to the reaction mixture, followed by ethyl acetate extraction. The organic layer was washed sequentially with water and brine and dried over magnesium sulfate, followed by concentration under reduced pressure. After filtration and concentration under reduced pressure, the resulting residue was washed with hexane and dried under reduced pressure to obtain the title compound (11 g) having the following physical properties.

TLC:Rf 0.38 (methylene chloride:methanol=9:1)
$^1$H-NMR (CDCl$_3$): δ 0.43-0.60, 2.25, 2.34, 4.10, 4.25, 6.95, 7.20, 7.29

Example 35

Ethyl (4-bromo-1-{[1-(2-ethoxy-2-oxoethyl)cyclopropyl]methyl}-2-methyl-1H-indol-3-yl)acetate To a solution of the compound (11 g) prepared in Example 34 in N,N-dimethylformamide (30 mL), potassium carbonate (14 g) and iodoethane (14 g) were added, followed by stirring at room temperature for 8 hours. Water was added under ice-cooling to the reaction mixture, followed by ethyl acetate extraction. The organic layer was washed sequentially with water and brine and dried over magnesium sulfate, followed by concentration under reduced pressure. After filtration and concentration under reduced pressure, the resulting residue was washed with diisopropylether and hexane, and dried under reduced pressure to obtain the title compound (12 g) having the following physical properties.

TLC:Rf 0.42 (hexane:ethyl acetate=2:1)
$^1$H-NMR (CDCl$_3$): δ 0.40-0.48, 1.24, 1.25, 2.28, 2.35, 4.01, 4.09-4.19, 4.32, 6.92, 7.18, 7.28

Example 36

[1-{[1-(carboxymethyl)cyclopropyl]methyl}-2-methyl-4-({4-[4-(pentafluorophenyl)butoxy]phenyl}ethynyl)-1H-indol-3-yl]acetic Acid By the same procedure as in Example 3→Example 4→Example 8→Example 9 using the compound prepared in Example 35 instead of the compound prepared in Example 2, the compound of the present invention having the following physical properties was obtained.

TLC:Rf 0.50 (methylene chloride:methanol=9:1)
$^1$H-NMR (DMSO-D$_6$): δ 0.23-0.44, 1.60-1.85, 2.23, 2.32, 2.76, 3.93-4.07, 4.34, 6.90-6.99, 6.99-7.07, 7.08-7.15, 7.41, 7.45-7.53, 12.13

Examples 36 (1) to (3)

By the same procedure as in Example 3→Example 4→Example 8→Example 9 using the compound prepared in Example 35 instead of the compound prepared in Example 2, and using the corresponding sulfonate instead of the compound prepared in Example 7, the compounds of the present invention having the following physical properties were obtained.

Example 36 (1)

[1-{[1-(carboxymethyl)cyclopropyl]methyl}-4-({4-[4-(4,5-difluoro-2-methylphenyl)butoxy]phenyl}ethynyl)-2-methyl-1H-indol-3-yl]acetic Acid TLC:Rf 0.24 (chloroform:methanol:water=10:1:0.1)
$^1$H-NMR (DMSO-D$_6$): δ 0.24-0.47, 1.56-1.86, 2.23, 2.33, 2.55-2.65, 3.96-4.10, 4.34, 6.93-6.99, 7.00-7.07, 7.07-7.14, 7.17-7.23, 7.41, 7.45-7.54, 12.12

Example 36 (2)

[1-{[1-(carboxymethyl)cyclopropyl]methyl}-2-methyl-4-({4-[4-(3,4,5-trifluorophenyl)butoxy]phenyl}ethynyl)-1H-indol-3-yl]acetic Acid TLC:Rf 0.36 (methylene chloride:methanol=9:1)
$^1$H-NMR (DMSO-D$_6$): δ 0.25-0.34, 0.37-0.43, 1.64-1.78, 2.23, 2.33, 2.60-2.68, 3.94-4.11, 4.35, 6.92-6.99, 7.04, 7.12, 7.16-7.27, 7.42, 7.47-7.55, 12.14

Example 36 (3)

(1-{[3-(carboxymethyl)-4-({4-[4-(3-chloro-2-methylphenyl)butoxy]phenyl}ethynyl)-2-methyl-1H-indol-1-yl]methyl}cyclopropyl)acetic Acid TLC:Rf 0.46 (methylene chloride:methanol=9:1)
$^1$H-NMR (DMSO-D$_6$): δ 0.26-0.36, 0.36-0.46, 1.56-1.89, 2.23, 2.31, 2.32, 2.65-2.75, 3.95-4.10, 4.34, 6.96, 7.03, 7.08-7.18, 7.21-7.29, 7.41, 7.50, 12.13

Example 37

4-[3-(carboxymethyl)-4-({4-[4-(3-chloro-2-methylphenyl)butoxy]phenyl}ethynyl)-7-fluoro-2-methyl-1H-indol-1-yl]butanoic Acid By the same procedure as in Example 2→Example 3→Example 4→Example 8→Example 9 using the compound prepared in Example 32 instead of the compound prepared in Example 1, and using the corresponding sulfonate instead of the compound prepared in Example 7, the compound of the present invention having the following physical properties was obtained.

TLC:Rf 0.24 (methylene chloride:methanol=9:1)
$^1$H-NMR (DMSO-D$_6$): δ 1.57-1.94, 2.24, 2.31, 2.33, 2.66-2.74, 3.96-4.08, 4.23, 6.87, 6.93-7.01, 7.05-7.18, 7.21-7.29, 7.43-7.56, 12.14

Example 37 (1)

4-[3-(carboxymethyl)-2-methyl-4-({4-[4-(2,3,4,5-tetrafluorophenyl)butoxy]phenyl}ethynyl)-1H-indol-1-yl]butanoic Acid By the same procedure as in Example 2→Example 3→Example 4→Example 8→Example 9 using the compound prepared in Example 32 instead of the compound prepared in Example 1, and using the corresponding sulfonate instead of the compound prepared in Example 7, the compound of the present invention having the following physical properties was obtained.

TLC:Rf 0.28 (methylene chloride:methanol=9:1)
$^1$H-NMR (DMSO-D$_6$): δ 1.67-1.78, 1.78-1.90, 2.24-2.31, 2.33, 2.65-2.76, 3.96-4.06, 4.10-6.92-6.99, 7.01-7.09, 7.10-7.16, 7.31-7.43, 7.43-7.47, 7.48-7.54, 12.13

Example 38

[1-{[1-(carboxymethyl)cyclopropyl]methyl}-4-({4-[4-(pentafluorophenyl)butoxy]phenyl}ethynyl)-1H-indol-3-yl]acetic Acid By the same procedure as in Example 29→Example 30→Example 31→Example 32→Example 33→Example 34→Example 35→Example 3→Example 4→Example 8→Example 9 using 4-bromo-1H-indole instead of the compound prepared in Example 28, the compound of the present invention having the following physical properties was obtained.

TLC:Rf 0.45 (methylene chloride:methanol=9:1)

$^1$H-NMR (DMSO-D$_6$): δ 0.46-0.54, 0.63-0.74, 1.60-1.86, 2.03, 2.76, 3.95-4.09, 4.18, 6.96, 7.07-7.22, 7.34, 7.41-7.48, 7.50, 12.17

Example 39

4-[3-(carboxymethyl)-4-({4-[4-(pentafluorophenyl)butoxy]phenyl}ethynyl)-1H-indol-1-yl]butanoic Acid By the same procedure as in Example 29→Example 30→Example 31→Example 32→Example 2→Example 3→Example 4→Example 8→Example 9 using 4-bromo-1H-indole instead of the compound prepared in Example 28, the compound of the present invention having the following physical properties was obtained.

TLC:Rf 0.39 (methylene chloride:methanol=9:1)

$^1$H-NMR (DMSO-D$_6$): δ 1.62-1.82, 1.88-2.04, 2.19, 2.76, 3.98, 4.02, 4.16, 6.90-6.99, 7.07-7.19, 7.31, 7.41-7.56, 12.13

Example 40

4-bromo-1-(phenylsulfonyl)-1H-pyrrolo[2,3-b]pyridine

To a solution of 4-bromo-1H-pyrrolo[2,3-b]pyridine (6.9 g, prepared according to the method described in Organic Letters, 2003, vol. 5, 5023-5025) and benzyltriethylammonium chloride (210 mg) in methylene chloride (150 mL), sodium hydroxide (4.3 g) and benzenesulfonyl chloride (5.5 mL) were added under ice-cooling. The reaction mixture was stirred at room temperature for 1 hour and filtered through "Celite" (registered trademark), and the filtrate was concentrated. The resulting residue was purified by a purification system CombiFlash CompanionXL (manufactured by Isco, Co., Ltd., column: RediSep 120 g; hexane:ethyl acetate=95:5→60:40) to obtain the title compound (9.8 g) having the following physical properties.

TLC:Rf 0.58 (hexane:ethyl acetate=2:1)

$^1$H-NMR (DMSO-D$_6$): δ 6.78, 7.56-7.67, 7.68-7.76, 8.05, 8.08-8.17, 8.21-8.27

Example 41

4-bromo-2-methyl-1-(phenylsulfonyl)-1H-pyrrolo[2,3-b]pyridine

Solution of diisopropylethylamine (7.8 mL) in tetrahydrofuran (60 mL) was cooled to −78° C. under an argon atmosphere, and n-butyl lithium (1.63M hexane solution, 34 mL) was added thereto, followed by stirring for 30 minutes. To the reaction mixture, a solution of the compound (9.3 g) prepared in Example 40 in tetrahydrofuran (60 mL) was added at −25° C., followed by stirring for 30 minutes. Solution of iodomethane (1.9 mL) in tetrahydrofuran (10 mL) was added thereto, followed by stirring for 2 hours. A saturated aqueous ammonium chloride solution (100 mL) was added to the reaction mixture, followed by quenching, dilution with water (200 mL), and extraction with ethyl acetate. The organic layer was dried over magnesium sulfate, and concentrated under reduced pressure. The resulting residue was purified by a purification system CombiFlash CompanionXL (manufactured by Isco, Co., Ltd., column: RediSep 120 g; hexane:ethyl acetate=100:0→80:20→70:30) to obtain the title compound (3.0 g) having the following physical properties.

TLC:Rf 0.38 (hexane:ethyl acetate=3:1)

$^1$H-NMR (CDCl$_3$): δ 2.75, 6.36, 7.31, 7.44-7.52, 7.54-7.62, 8.10-8.20

Example 42

4-bromo-2-methyl-1H-pyrrolo[2,3-b]pyridine

Tetrabutylammonium fluoride (1.0M tetrahydrofuran solution, 17 mL) was added under ice-cooling to a solution of the compound (3.0 g) prepared in Example 41 in tetrahydrofuran (8.0 mL), followed by stirring at room temperature for 4 hours. The reaction mixture was concentrated under reduced pressure. A saturated aqueous ammonium chloride solution was added to the resulting residue, followed by ethyl acetate extraction. The organic layer was dried over magnesium sulfate, and concentrated under reduced pressure. The resulting residue was purified by a purification system CombiFlash CompanionXL (manufactured by Isco, Co., Ltd., column: RediSep 40 g; hexane:ethyl acetate=90:10→80:20→70:30) to obtain the title compound (590 mg) having the following physical properties.

TLC:Rf 0.14 (hexane:ethyl acetate=3:1)

$^1$H-NMR (CDCl$_3$): δ 2.54, 6.24, 7.23, 8.00, 10.98

Example 43

1-(4-bromo-2-methyl-1H-pyrrolo[2,3-b]pyridin-3-yl)-N,N-dimethylmethanamine

N,N-dimethylmethyleneammonium chloride (410 mg) was added to a solution of the compound (590 mg) prepared in Example 42 in n-butyl alcohol (10 mL), followed by stirring at 135° C. for 1 hour, and cooling to room temperature. To the reaction mixture tert-butyl methyl ether and 1N hydrochloric acid were added, followed by separation of the organic layer. Thereafter, the aqueous layer was extracted with tert-butyl methyl ether. The aqueous layer was neutralized under ice-cooling with a 5N aqueous sodium hydroxide solution, and the aqueous layer was extracted with methylene chloride. The organic layer was dried over magnesium sulfate and concentrated under reduced pressure to obtain the title compound (510 mg) having the following physical properties.

TLC:Rf 0.09 (methylene chloride:methanol=9:1)

$^1$H-NMR (CDCl$_3$): δ 2.32, 2.51, 3.69, 7.23, 7.96, 10.69

Example 44

(4-bromo-2-methyl-1H-pyrrolo[2,3-b]pyridin-3-yl)acetonitrile

Dimethyl sulfate (0.41 mL) was added under ice-cooling to a solution of the compound (510 mg) prepared in Example 43 in tetrahydrofuran (7.5 mL), followed by stirring at room temperature for 1 hour. The supernatant was discarded by decantation, and the solid was washed with tetrahydrofuran, followed by drying under reduced pressure. Water (7.5 mL) and potassium cyanide (200 mg) were added thereto, followed by stirring at 75° C. for 4 hours. The reaction mixture was filtered and washed with water, followed by during under reduced pressure to obtain the title compound (270 mg) having the following physical properties.

TLC:Rf 0.18 (hexane:ethyl acetate=1:1)

$^1$H-NMR (DMSO-D$_6$): δ 2.40, 4.09, 7.28, 7.97, 12.03

Example 45

Ethyl (4-bromo-2-methyl-1H-pyrrolo[2,3-b]pyridin-3-yl)acetate

Chlorotrimethylsilane (1.4 mL) was added under ice-cooling to a solution of the compound (270 mg) prepared in Example 44 in ethanol (5.0 mL), followed by stirring at 80° C. for 4 hours. Sulfuric acid (0.10 mL) was added thereto, followed by stirring for 2.5 hours. Dimethoxyethane (4.0 mL) was added to the reaction mixture, followed by stirring at 80° C. for 15 hours, and sulfuric acid (0.10 mL) was added thereto, followed by stirring for 20 hours. The reaction mixture was diluted with a saturated aqueous sodium hydrogen carbonate solution, and extracted with ethyl acetate. The organic layer was dried over magnesium sulfate, and concentrated under reduced pressure to obtain the title compound (280 mg) having the following physical properties.

TLC:Rf 0.44 (methylene chloride:methanol=9:1)
$^1$H-NMR (DMSO-$D_6$): δ 1.17, 2.31, 3.85, 4.07, 7.20, 7.91, 11.80

Example 46

4-[3-(carboxymethyl)-2-methyl-4-({4-[4-(pentafluorophenyl)butoxy]phenyl}ethynyl)-1H-pyrrolo[2,3-b]pyridin-1-yl]butanoic Acid By the same procedure as in Example 2→Example 3→Example 4→Example 8→Example 9 using the compound prepared in Example 45 instead of the compound prepared in Example 1, the compound of the present invention having the following physical properties was obtained.

TLC:Rf 0.25 (methylene chloride:methanol=9:1)
$^1$H-NMR (DMSO-$D_6$): δ 1.62-1.81, 1.82-1.96, 2.23, 2.40, 2.76, 3.96, 4.04, 4.25, 6.94-7.04, 7.09, 7.52-7.61, 8.11, 12.17

Example 47

Ethyl 4-[7-{(E)-2-[4-(acetyloxy)phenyl]vinyl}-1-(2-ethoxy-2-oxoethyl)-2-methyl-1H-indol-3-yl]butanoate To a solution of the compound (250 g) prepared in Example 10 in 1,4-dioxane (2.5 L), 4-vinyl phenylacetate (110 g), dicyclohexylmethylamine (150 g), tris (dibenzylideneacetone)dipalladium (57 g), and tri-tert-butylphosphine (25 g) were added, followed by stirring at 100° C. for 2 hours. The reaction mixture was filtered through "Celite" (registered trademark), and the filtrate was concentrated under reduced pressure. The resulting residue was purified by silica gel column chromatography (hexane:ethyl acetate=5:1→6:4), and solidified with hexane to obtain the title compound (210 g) having the following physical properties.

TLC:Rf 0.44 (hexane:ethyl acetate=2:1)
$^1$H-NMR (CDCl$_3$): δ 1.22, 1.24, 1.94, 2.37-2.28, 2.30, 2.32, 2.76, 4.10, 4.20, 4.96, 6.85, 7.12-7.04, 7.16, 7.58-7.44

Example 48

4-{1-(carboxymethyl)-2-methyl-7-[(E)-2-{4-[4-(2,3,4,6-tetrafluorophenyl)butoxy]phenyl}vinyl]-1H-indol-3-yl}butanoic acid By the same procedure as in Example 4→Example 8→Example 9 using the compound prepared in Example 47 instead of the compound prepared in Example 3, and using the corresponding sulfonate instead of the compound prepared in Example 7, the compound of the present invention having the following physical properties was obtained.

TLC:Rf 0.49 (methylene chloride:methanol=9:1)
$^1$H-NMR (DMSO-$D_6$): δ 1.60-1.84, 2.21, 2.25, 2.61-2.77, 3.99, 4.99, 6.82-6.94, 6.98, 7.14, 7.38, 7.41-7.58

Example 48 (1)

4-{1-(carboxymethyl)-7-[(E)-2-{4-[4-(3-chloro-2-methylphenyl)butoxy]phenyl}vinyl]-2-methyl-1H-indol-3-yl}butanoic Acid By the same procedure as in Example 4→Example 8→Example 9 using the compound prepared in Example 47 instead of the compound prepared in Example 3, and using the corresponding sulfonate instead of the compound prepared in Example 7, the compound of the present invention having the following physical properties was obtained.

TLC:Rf 0.44 (methylene chloride:methanol:acetic acid=90:10:1)
$^1$H-NMR (DMSO-$D_6$): δ 1.52-1.86, 2.21, 2.25, 2.31, 2.61-2.79, 4.02, 5.01, 6.81-7.05, 7.07-7.19, 7.22-7.31, 7.34-7.43, 7.43-7.59

Example 49

4-{3-(carboxymethyl)-2-methyl-4-[(E)-2-{4-[4-(3,4,5-trifluorophenyl)butoxy]phenyl}vinyl]-1H-indol-1-yl}butanoic Acid By the same procedure as in Example 2→Example 47→Example 4→Example 8→Example 9 using the compound prepared in Example 32 instead of the compound prepared in Example 1, and using the corresponding sulfonate instead of the compound prepared in Example 7, the compound of the present invention having the following physical properties was obtained.

TLC:Rf 0.36 (methylene chloride:methanol=9:1)
$^1$H-NMR (DMSO-$D_6$): δ 1.66-1.76, 1.78-1.90, 2.28, 2.36, 2.64, 3.77, 3.92-4.05, 4.12, 6.77-7.41, 7.52, 7.72, 12.25

Example 50

(1-{[1-(carboxymethyl)cyclopropyl]methyl}-4-[(E)-2-{4-[4-(pentafluorophenyl)butoxy]phenyl}vinyl]-1H-indol-3-yl)acetic Acid By the same procedure as in Example 29→Example 30→Example 31→Example 32→Example 33→Example 34→Example 35→Example 47→Example 4→Example 8→Example 9 using 4-bromo-1H-indole instead of the compound prepared in Example 28, the compound of the present invention having the following physical properties was obtained.

TLC:Rf 0.33 (methylene chloride:methanol=9:1)
$^1$H-NMR (DMSO-$D_6$): δ 0.45-0.52, 0.62-0.69, 1.63-1.82, 2.05, 2.76, 3.85, 4.01, 4.15, 6.92, 7.00-7.16, 7.24-7.37, 7.52, 7.62, 12.26

Example 50 (1)

(1-{[1-(carboxymethyl)cyclopropyl]methyl}-4-[(E)-2-{4-[4-(3,4,5-trifluorophenyl)butoxy]phenyl}vinyl]-1H-indol-3-yl)acetic Acid By the same procedure as in Example 29→Example 30→Example 31→Example 32→Example 33→Example 34→Example 35→Example 47→Example 4→Example 8→Example 9 using 4-bromo-1H-indole instead of the compound prepared in Example 28, and using the corresponding sulfonate instead of the compound prepared in Example 7, the compound of the present invention having the following physical properties was obtained.

TLC:Rf 0.51 (chloroform:methanol:water=40:8:1)

$^1$H-NMR (DMSO-D$_6$): δ 0.41-0.73, 1.62-1.80, 2.05, 2.65, 3.84, 3.93-4.06, 4.15, 6.87-6.96, 6.99-7.37, 7.51, 7.62, 12.25

Example 51

Ethyl 4-[7-bromo-1-(2-ethoxy-2-oxoethyl)-1H-indol-3-yl]butanoate

By the same procedure as in Example 2 using the compound prepared in Example 23 instead of the compound prepared in Example 1, and using ethyl bromoacetate instead of ethyl 4-bromobutyrate, the title compound having the following physical properties was obtained.

TLC:Rf 0.32 (hexane:ethyl acetate=4:1)

$^1$H-NMR (CDCl$_3$): δ 1.22-1.28, 1.95-2.07, 2.36, 2.75, 4.12, 4.23, 5.21, 6.79, 6.93, 7.32, 7.51

Example 52

4-{1-(carboxymethyl)-7-[(E)-2-{4-[4-(3,4,5-trifluorophenyl)butoxy]phenyl}vinyl]-1H-indol-3-yl}butanoic Acid By the same procedure as in Example 47→Example 4→Example 8→Example 9 using the compound prepared in Example 51 instead of the compound prepared in Example 10, and using the corresponding sulfonate instead of the compound prepared in Example 7, the compound of the present invention having the following physical properties was obtained.

TLC:Rf 0.60 (methylene chloride:methanol:acetic acid=90:10:1)

$^1$H-NMR (DMSO-D$_6$): δ 1.61-1.77, 1.78-1.92, 2.28, 2.58-2.71, 3.92-4.10, 5.12, 6.86-6.96, 7.02, 7.08, 7.15-7.30, 7.37-7.61, 11.67-13.79

Example 53

(3-{[1-(carboxymethyl)cyclopropyl]methyl}-7-[(E)-2-{4-[4-(3-fluoro-2-methylphenyl)butoxy]phenyl}vinyl]-2-methyl-1H-indol-1-yl)acetic Acid By the same procedure as in Example 47→Example 4→Example 8→Example 9 using the compound prepared in Example 20 instead of the compound prepared in Example 10, and using the corresponding sulfonate instead of the compound prepared in Example 7, the compound of the present invention having the following physical properties was obtained.

TLC:Rf 0.60 (chloroform:methanol:acetic acid=85:15:1)

$^1$H-NMR (DMSO-D$_6$): δ 0.23-0.39, 1.58-1.87, 2.17, 2.18, 2.24, 2.62-2.72, 2.88, 4.02, 5.01, 6.87, 6.91-7.06, 7.08-7.19, 7.39, 7.44-7.56, 12.05, 12.93-13.35

Example 54

4,4'-[2-methyl-7-({4-[4-(pentafluorophenyl)butoxy]phenyl}ethynyl)-1H-indole-1,3-diyl]dibutanoic Acid

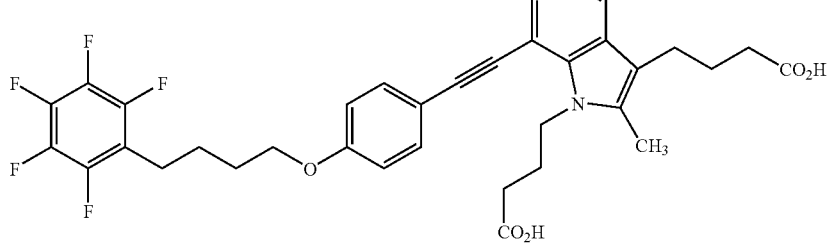

The compound (50 mg) prepared in Example 9 was dissolved in methyl tertiary butyl ether (1.5 mL) at 50° C.

To the solution, n-heptane (0.75 mL) was added at room temperature, which was then allowed to stand for 30 minutes. The precipitated solid was filtered and dried under reduced pressure to obtain the title compound (39 mg).

Figure 2:
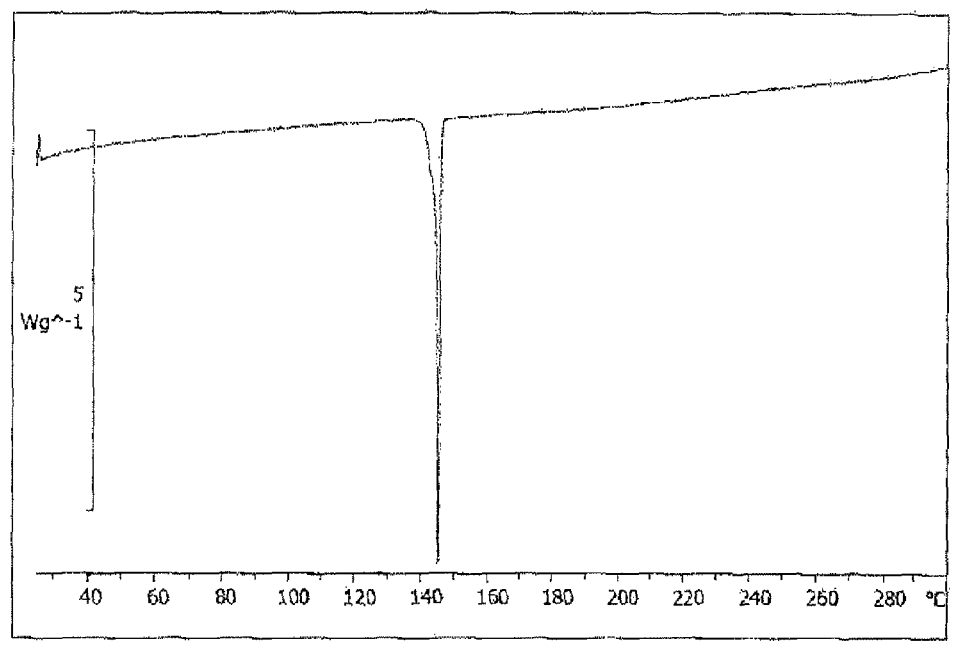
FIG. 2 shows a chart of differential scanning calorimetry (DSC) of a crystal of 4,4'-[2-methyl-7-({4-[4-(pentafluorophenyl)butoxy]phenyl}ethynyl)-1H-indole-1,3-diyl]dibutanoic acid.

The powdered X-ray diffraction spectrum and differential scanning calorimetry (DSC) data of the crystal measured under the following conditions are respectively shown in FIG. 1 and FIG. 2.

[1] Powdered X-Ray Diffraction Spectrum

| Apparatus: | BRUKER axs, D8 DISCOVER with GADDS |
|---|---|
| Target: | Cu |
| Voltage: | 40 kV |
| Current: | 40 mA |

The crystal can be characterized by the powdered X-ray diffraction spectrum obtained with Cu—Kα radiation with the diffraction angle (2θ) and relative intensity as shown in Table 1 below.

TABLE 1

| Diffraction angle (2θ) | Relative intensity |
| --- | --- |
| 8.45 | 25 |
| 9.23 | 98 |
| 9.95 | 19 |
| 11.88 | 44 |
| 13.14 | 20 |
| 13.82 | 26 |
| 14.63 | 44 |
| 15.00 | 23 |
| 15.52 | 100 |
| 16.11 | 15 |
| 16.78 | 38 |
| 17.88 | 18 |

TABLE 1-continued

| Diffraction angle (2θ) | Relative intensity |
| --- | --- |
| 18.54 | 23 |
| 19.60 | 49 |
| 19.94 | 24 |
| 20.71 | 23 |
| 21.11 | 63 |
| 21.74 | 88 |
| 22.76 | 21 |
| 23.26 | 22 |
| 23.68 | 48 |
| 24.28 | 49 |
| 24.73 | 45 |

[2] Differential Scanning Calorimetry (DSC)

| Apparatus: | METTLER TOLEDO, DSC822e |
| --- | --- |
| Amount of Sample: | 1.37 mg |
| Sample Cell: | Aluminum pan (40 μL) |
| Flow Rate of N$_2$ Gas: | 40 mL/min |
| Programming Rate: | 5° C./min (Scan range: 25-300° C.) |

Example 54 (1)

Dimethyl 4,4'-[2-methyl-7-({4-[4-(pentafluorophenyl)butoxy]phenyl}ethynyl)-1H-indole-1,3-diyl]dibutanoate By the same procedure as in Example 2→Example 3→Example 4→Example 8 using methyl 4-(7-bromo-2-methyl-1H-indol-3-yl)butanoate (which was prepared by the procedure as in Example 1 using methanol instead of ethanol) instead of the compound prepared in Example 1, and using methyl 4-bromobutyrate instead of ethyl 4-bromobutyrate, the title compound having the following physical properties was obtained.

TLC:Rf 0.40 (hexane:ethyl acetate=3:1)
$^1$H-NMR (CDCl$_3$): δ 1.72-2.00, 2.06-2.20, 2.26-2.40, 2.68-2.84, 3.61, 3.64, 4.01, 4.63, 6.88, 7.01, 7.30, 7.40-7.50

The compound of the present invention of Example 9 can also be prepared by the same procedure as in Example 9 using the compound of Example 54 (1) instead of the compound prepared in Example 8.

Example 55

4,4'-[4-fluoro-7-({4-[4-(3-fluoro-2-methylphenyl)butoxy]phenyl}ethynyl)-2-methyl-1H-indole-1,3-diyl]dibutanoic Acid

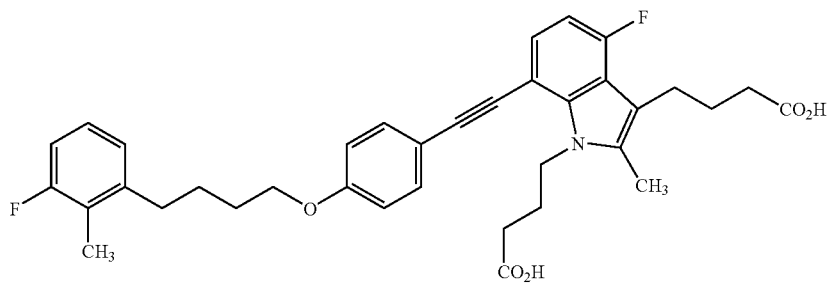

The compound (30 mg) prepared in Example 14 (2) was dissolved in methyl tertiary butyl ether (2.4 mL) at 60° C. The solution was cooled to room temperature to induce crystallization. The precipitated solid was filtered and dried under reduced pressure to obtain the title compound (24 mg).

Figure 3:
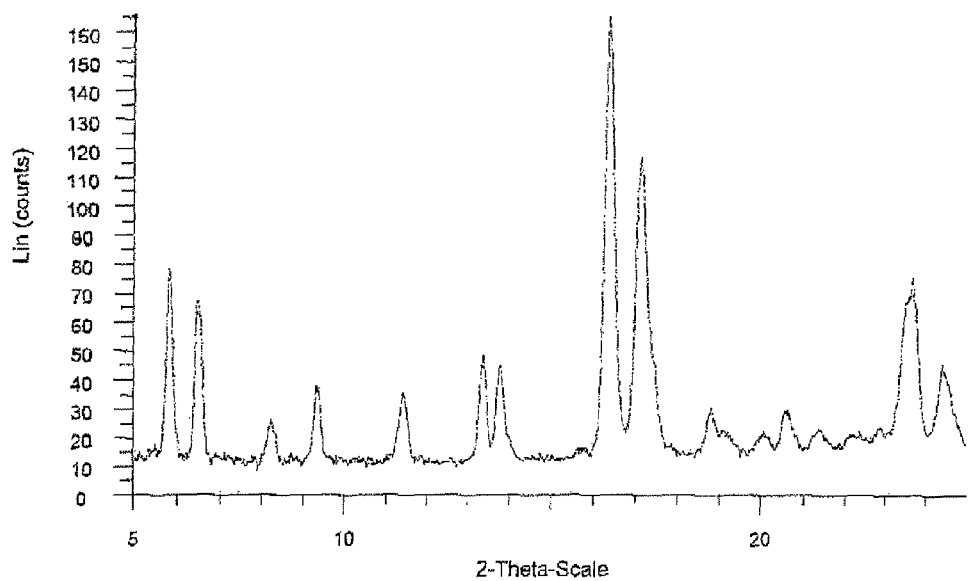
FIG. 3 shows a chart of powdered X-ray diffraction spectrum of a crystal of 4,4'-[4-fluoro-7-({4-[4-(3-fluoro-2-methylphenyl)butoxy]phenyl}ethynyl)-2-methyl-1H-indole-1,3-diyl]dibutanoic acid.
Figure 4:
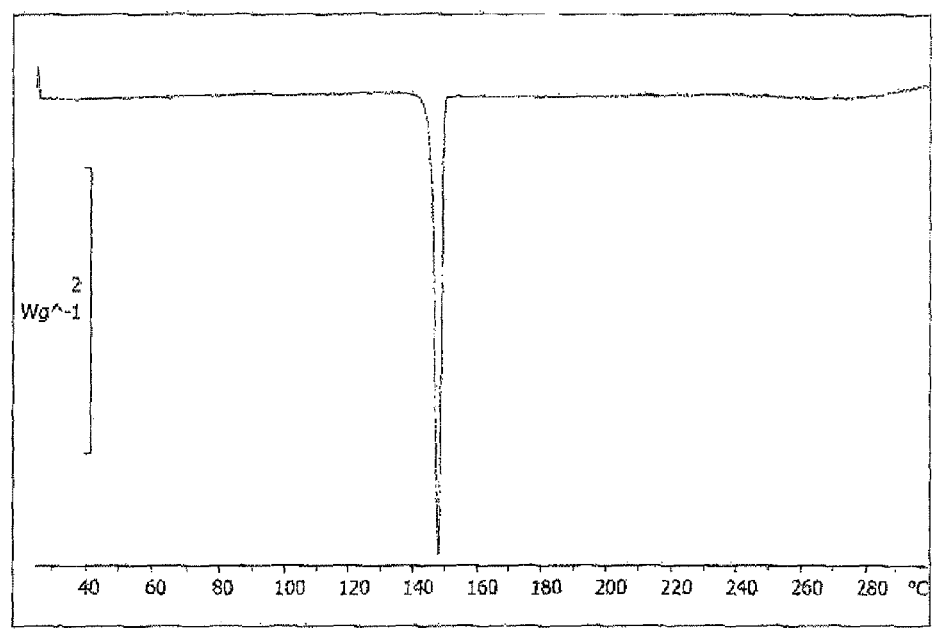
FIG. 4 shows a chart of differential scanning calorimetry (DSC) of a crystal of 4,4'-[4-fluoro-7-({4-[4-(3-fluoro-2-methylphenyl)butoxy]phenyl}ethynyl)-2-methyl-1H-indole-1,3-diyl]dibutanoic acid.

The powdered X-ray diffraction spectrum and differential scanning calorimetry (DSC) data of the crystal measured under the following conditions are respectively shown in FIG. 3 and FIG. 4.

[1] Powdered X-Ray Diffraction Spectrum

| Apparatus: | BRUKER axs, D8 DISCOVER with GADDS |
| --- | --- |
| Target: | Cu |
| Voltage: | 40 kV |
| Current: | 40 mA |

The crystal can be characterized by the powdered X-ray diffraction spectrum obtained with Cu—Kα radiation with the diffraction angle (2θ) and relative intensity as shown in Table 2 below.

TABLE 2

| Diffraction angle (2θ) | Relative intensity |
| --- | --- |
| 5.81 | 47 |
| 6.49 | 41 |
| 8.23 | 16 |
| 9.33 | 23 |
| 11.42 | 22 |
| 13.36 | 29 |
| 13.77 | 27 |
| 16.38 | 100 |
| 17.13 | 71 |
| 18.81 | 19 |
| 20.61 | 18 |
| 23.69 | 46 |
| 24.43 | 26 |

[2] Differential Scanning Calorimetry (DSC)

| Apparatus: | METTLER TOLEDO, DSC822e |
|---|---|
| Amount of Sample: | 3.30 mg |
| Sample Cell: | Aluminum pan (40 μL) |
| Flow Rate of $N_2$ Gas: | 40 mL/min |
| Programming Rate: | 5° C./min (Scan range: 25-300° C.) |

Example 55 (1)

Dimethyl 4,4'-[4-fluoro-7-({4-[4-(3-fluoro-2-methylphenyl)butoxy]phenyl}ethynyl)-2-methyl-1H-indole-1,3-diyl]dibutanoate By the same procedure as in Example 2→Example 3→Example 4→Example 8 using methyl 4-(7-bromo-4-fluoro-2-methyl-1H-indol-3-yl)butanoate (which was prepared by the procedure as in Example 1 using (2-bromo-5-fluorophenyl)hydrazine instead of (2-bromophenyl)hydrazine hydrochloride, and using methanol instead of ethanol) instead of the compound prepared in Example 1; using methyl 4-bromobutyrate instead of ethyl 4-bromobutyrate; and using 4-(3-fluoro-2-methylphenyl)butyl 4-methylbenzene sulfonate instead of the compound prepared in Example 7, the title compound having the following physical properties was obtained.

TLC:Rf 0.36 (hexane:ethyl acetate=3:1)

$^1$H-NMR (CDCl$_3$): δ 1.70-2.00, 2.10-2.20, 2.23, 2.30-2.40, 2.70, 2.82, 3.62, 3.63, 4.02, 4.62, 6.67, 6.85-6.92, 6.94, 7.05-7.10, 7.21, 7.44

The compound of the present invention of Example 14 (2) can also be prepared by the same procedure as in Example 9 using the compound of Example 55 (1) instead of the compound prepared in Example 8.

Example 56

4,4'-[4-fluoro-2-methyl-7-({4-[4-(2,3,4,6-tetrafluorophenyl)butoxy]phenyl}ethynyl)-1H-indole-1,3-diyl]dibutanoic Acid

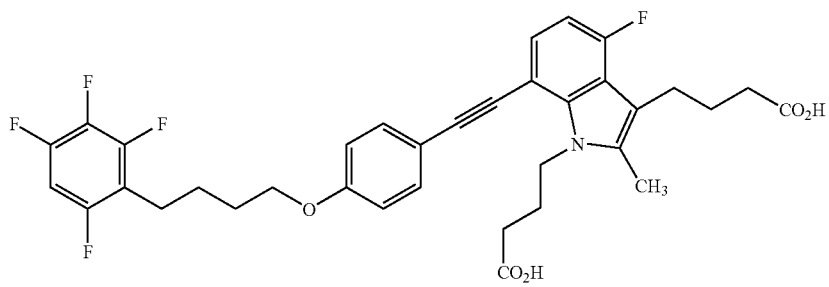

The compound (50 mg) prepared in Example 14 (3) was dissolved in ethyl acetate (1.4 mL) at 70° C. To the solution, n-heptane (0.68 mL) was added at room temperature, which was then cooled to 0° C. The precipitated solid was filtered and dried under reduced pressure to obtain the title compound (39 mg).

Figure 5:
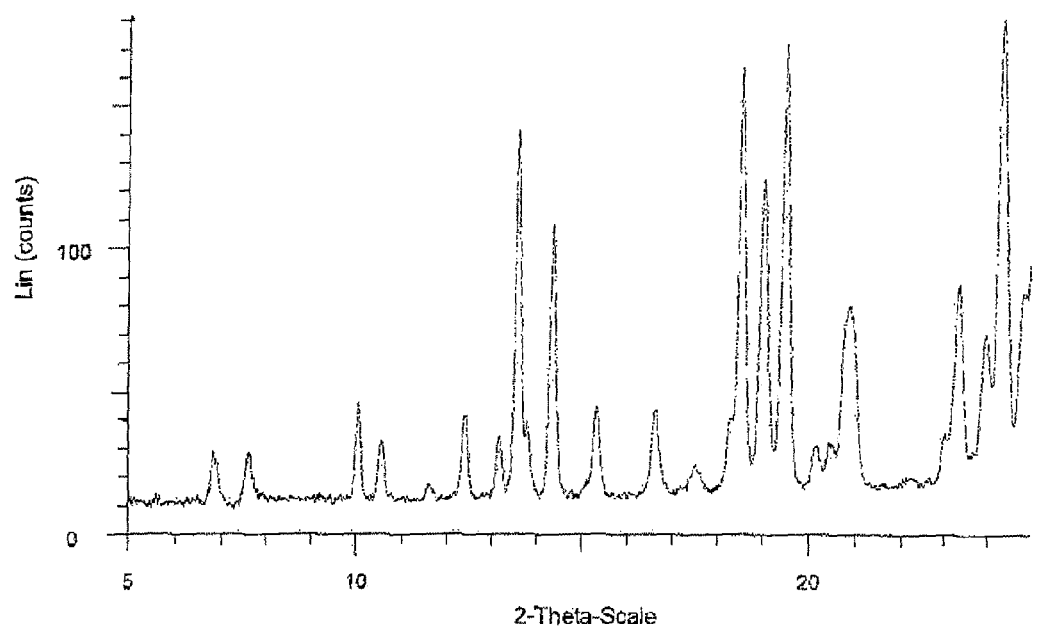
FIG. 5 shows a chart of powdered X-ray diffraction spectrum of a crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid.
Figure 6:
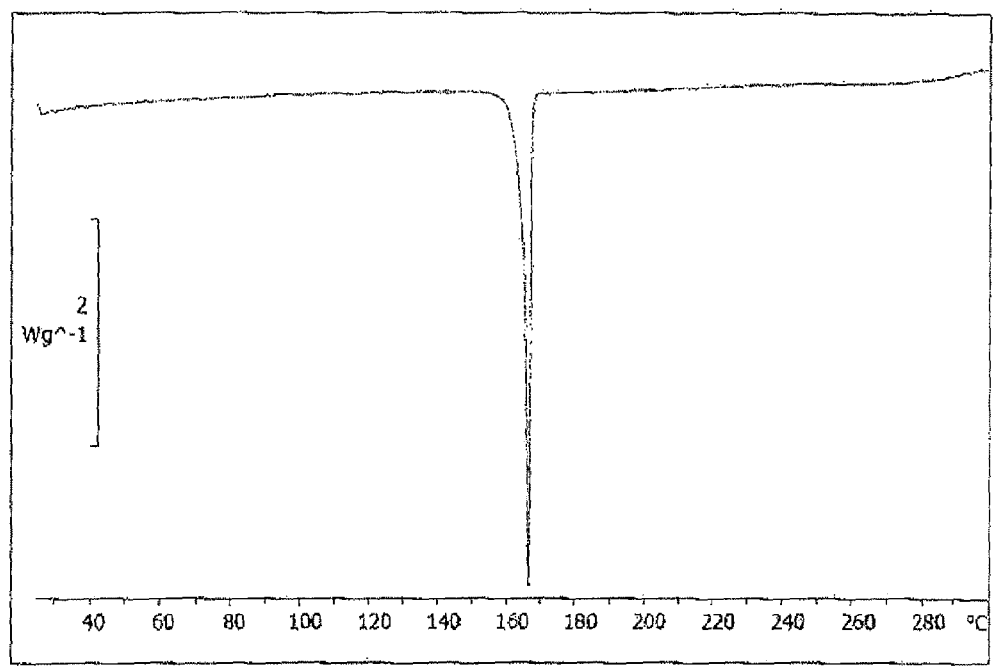
FIG. 6 shows a chart of differential scanning calorimetry (DSC) of a crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid.

The powdered X-ray diffraction spectrum and differential scanning calorimetry (DSC) data of the crystal measured under the following conditions are respectively shown in FIG. 5 and FIG. 6.

[1] Powdered X-Ray Diffraction Spectrum

| Apparatus: | BRUKER axs, D8 DISCOVER with GADDS |
|---|---|
| Target: | Cu |
| Voltage: | 40 kV |
| Current: | 40 mA |

The crystal can be characterized by the powdered X-ray diffraction spectrum obtained with Cu—Kα radiation with the diffraction angle (2θ) and relative intensity as shown in Table 3 below.

TABLE 3

| Diffraction angle (2θ) | Relative intensity |
|---|---|
| 6.85 | 16 |
| 7.61 | 16 |
| 10.03 | 26 |
| 10.54 | 18 |
| 12.40 | 23 |
| 13.17 | 19 |
| 13.57 | 78 |
| 14.35 | 60 |
| 15.33 | 25 |
| 16.64 | 24 |
| 18.24 | 21 |
| 18.53 | 91 |
| 19.03 | 69 |
| 19.49 | 96 |
| 20.15 | 17 |
| 20.48 | 18 |
| 20.88 | 44 |
| 23.04 | 20 |
| 23.35 | 49 |
| 23.97 | 39 |
| 24.32 | 100 |
| 24.83 | 47 |

[2] Differential Scanning Calorimetry (DSC)

| Apparatus: | METTLER TOLEDO, DSC822e |
|---|---|
| Amount of Sample: | 4.70 mg |

-continued

| Sample Cell: | Aluminum pan (40 μL) |
|---|---|
| Flow Rate of $N_2$ Gas: | 40 mL/min |
| Programming Rate: | 5° C./min (Scan range: 25-300° C.) |

Example 56 (1)

Dimethyl 4,4'-[4-fluoro-2-methyl-7-({4-[4-(2,3,4,6-tetrafluorophenyl)butoxy]phenyl}ethynyl)-1H-indole-1,3-diyl]dibutanoate By the same procedure as in Example 2→Example 3→Example 4→Example 8 using methyl 4-(7-bromo-4-fluoro-2-methyl-1H-indol-3-yl)butanoate instead of the compound prepared in Example 1; using methyl 4-bromobutyrate instead of ethyl 4-bromobutyrate; and using 4-(2,3,4,6-tetrafluorophenyl)butyl 4-methylbenzene sulfonate instead of the compound prepared in Example 7, the title compound having the following physical properties was obtained.

TLC:Rf 0.39 (hexane:ethyl acetate=3:1)
$^1$H-NMR (CDCl$_3$): δ 1.70-2.00, 2.06-2.20, 2.26-2.38, 2.74, 2.81, 3.62, 3.63, 4.00, 4.62, 6.66, 6.69-6.80, 6.87, 7.20, 7.43

The compound of the present invention of Example 14 (3) can also be prepared by the same procedure as in Example 9 using the compound of Example 56 (1) instead of the compound prepared in Example 8.

Example 57

Disodium 4,4'-[2-methyl-7-({4-[4-(pentafluorophenyl)butoxy]phenyl}ethynyl)-1H-indole-1,3-diyl]dibutanoate A 0.1 mol/L aqueous sodium hydroxide solution (0.33 mL) was added to a solution of the compound (10 mg) prepared in Example 9 in tetrahydrofuran (0.10 mL). The mixture was concentrated under reduced pressure to obtain the title compound having the following physical properties.

$^1$H-NMR (METHANOL-D$_4$): δ 1.71-1.93, 2.00-2.15, 2.16-2.26, 2.41, 2.73, 2.78-2.86, 4.03, 4.56-4.66, 6.88-6.96, 7.18, 7.44-7.52

Example 58

Disodium 4,4'-[4-fluoro-7-({4-[4-(3-fluoro-2-methylphenyl)butoxy]phenyl}ethynyl)-2-methyl-1H-indole-1,3-diyl]dibutanoate By the same procedure as in Example 57 using the compound prepared in Example 14 (2) instead of the compound prepared in Example 9, the title compound having the following physical properties was obtained.

$^1$H-NMR (METHANOL-D$_4$): δ 1.68-1.95, 2.00-2.13, 2.15-2.25, 2.40, 2.68-2.76, 2.80, 4.03, 4.56-4.67, 6.60, 6.80-6.88, 6.89-6.99, 7.04-7.17, 7.47

Example 59

Disodium 4,4'-[4-fluoro-2-methyl-7-({4-[4-(2,3,4,6-tetrafluorophenyl)butoxy]phenyl}ethynyl)-1H-indole-1,3-diyl]dibutanoate By the same procedure as in Example 57 using the compound prepared in Example 14 (3) instead of the compound prepared in Example 9, the title compound having the following physical properties was obtained.

$^1$H-NMR (METHANOL-D$_4$): δ 1.70-1.95, 1.98-2.13, 2.15-2.25, 2.40, 2.70-2.85, 4.02, 4.57-4.68, 6.60, 6.91, 6.96-7.08, 7.12, 7.46

Example 60

Bis(2,6-diammoniohexanoate) 4,4'-[2-methyl-7-({4-[4-(pentafluorophenyl)butoxy]phenyl}ethynyl)-1H-indole-1,3-diyl]dibutanoate A 0.1 mol/L lysine solution (0.33 mL) was added to a solution of the compound (10 mg) prepared in Example 9 in tetrahydrofuran (0.10 mL). The mixture was concentrated under reduced pressure to obtain the title compound having the following physical properties.

$^1$H-NMR (METHANOL-D$_4$): δ 1.39-1.56, 1.57-1.74, 1.74-1.98, 1.99-2.14, 2.15-2.27, 2.40, 2.69-2.85, 2.86-2.93, 3.52, 3.96-4.08, 4.58-4.69, 6.89-6.99, 7.19, 7.39-7.54

Example 61

Bis(2,6-diammoniohexanoate) 4,4'-[4-fluoro-7-({4-[4-(3-fluoro-2-methylphenyl)butoxy]phenyl}ethynyl)-2-methyl-1H-indole-1,3-diyl]dibutanoate By the same procedure as in Example 60 using the compound prepared in Example 14 (2) instead of the compound prepared in Example 9, the title compound having the following physical properties was obtained.

$^1$H-NMR (METHANOL-D$_4$): δ 1.40-1.56, 1.58-1.95, 2.01-2.14, 2.15-2.25, 2.39, 2.68-2.76, 2.81, 2.86-2.93, 3.53, 4.04, 4.60-4.68, 6.62, 6.81-6.88, 6.90-6.99, 7.03-7.11, 7.14, 7.46

Example 62

Bis(2,6-diammoniohexanoate) 4,4'-[4-fluoro-2-methyl-7-({4-[4-(2,3,4,6-tetrafluorophenyl)butoxy]phenyl}ethynyl)-1H-indole-1,3-diyl]dibutanoate By the same procedure as in Example 60 using the compound prepared in Example 14 (3) instead of the compound prepared in Example 9, the title compound was obtained.

Example 63

Disodium 4,4'-[2-methyl-7-({4-[4-(pentafluorophenyl)butoxy]phenyl}ethynyl)-1H-indole-1,3-diyl]dibutanoate Trihydrate The compound (10 g) prepared in Example 57 was dissolved in water (40 mL) and methanol (40 mL) at 53° C. To the solution, 2-propanol (1900 mL) was added and cooled to 5° C. The precipitated solid was filtered and dried at 40° C. under reduced pressure. The compound was maintained at 60% of relative humidity at 25° C. for 2 days to obtain the title compound (8.2 g) having the following physical properties.

$^1$H-NMR (METHANOL-D$_4$): δ 1.72-1.92, 2.01-2.14, 2.16-2.25, 2.41, 2.73, 2.77-2.87, 4.03, 4.58-4.67, 6.87-6.96, 7.18, 7.45-7.52

Example 64

Disodium 4,4'-[4-fluoro-7-({4-[4-(3-fluoro-2-methylphenyl)butoxy]phenyl}ethynyl)-2-methyl-1H-indole-1,3-diyl]dibutanoate Octahydrate The compound (10 g) prepared in Example 58 was dissolved in water (20 mL) and methanol (20 mL) at 53° C. To the solution, acetone (750 mL) was added and cooled to 15°

C. The precipitated solid was filtered and dried at 40° C. under reduced pressure. The compound was maintained at 75% of relative humidity at 40° C. for 10 days to obtain the title compound (8.2 g) having the following physical properties.

$^1$H-NMR (METHANOL-D$_4$): δ 1.68-1.95, 2.00-2.13, 2.15-2.25, 2.40, 2.68-2.76, 2.80, 4.04, 4.56-4.68, 6.61, 6.80-6.88, 6.89-6.99, 7.04-7.17, 7.47

Example 65

Disodium 4,4'-[4-fluoro-2-methyl-7-({4-[4-(2,3,4,6-tetrafluorophenyl)butoxy]phenyl}ethynyl)-1H-indole-1,3-diyl]dibutanoate Hydrate The compound (8.5 g) prepared in Example 59 was dissolved in water (22 mL) and methanol (22 mL) at 60° C. To the solution, acetone (430 mL) was added at room temperature and cooled to 2° C. The precipitated solid was filtered and dried at 50° C. under reduced pressure to obtain the title compound (7.8 g) having the following physical properties.

$^1$H-NMR (METHANOL-D$_4$): δ 1.67-1.96, 2.00-2.14, 2.15-2.25, 2.39, 2.69-2.85, 3.99, 4.56-4.68, 6.60, 6.91, 6.94-7.06, 7.12, 7.45

Comparative Example 1

4,4'-{2-methyl-7-[(E)-2-{4-[4-(pentafluorophenyl)butoxy]phenyl}vinyl]-1H-indole-1,3-diyl}dibutanoic Acid By the same procedure as in Example 47→Example 4→Example 8→Example 9 using the compound prepared in Example 2 instead of the compound prepared in Example 10, and using the corresponding sulfonate instead of the compound prepared in Example 7, the comparative compound having the following physical properties was obtained.

TLC:Rf 0.69 (chloroform:methanol=6:1)
$^1$H-NMR (DMSO-D$_6$): δ 1.62-1.81, 1.81-1.94, 2.19, 2.31, 2.60-2.84, 3.90-4.08, 4.19-4.32, 6.82-7.02, 7.13, 7.31-7.43, 7.54, 7.69, 11.91-12.21

Comparative Example 2

4,4'-{4-fluoro-7-[(E)-2-{4-[4-(3-fluoro-2-methylphenyl)butoxy]phenyl}vinyl]-2-methyl-1H-indole-1,3-diyl}dibutanoic Acid By the same procedure as in Example 47→Example 4→Example 8→Example 9 using diethyl 4,4'-(7-bromo-4-fluoro-2-methyl-1H-indole-1,3-diyl)dibutanoate (which was prepared by the same procedure as in Example 1→Example 2 using (2-bromo-5-fluorophenyl)hydrazine instead of (2-bromo phenyl)hydrazine hydrochloride) instead of the compound prepared in Example 10, and using the corresponding sulfonate instead of the compound prepared in Example 7, the comparative compound having the following physical properties was obtained.

TLC:Rf 0.44 (methylene chloride:methanol=9:1)
$^1$H-NMR (DMSO-D$_6$): δ 1.57-1.95, 2.13-2.25, 2.17, 2.30, 2.60-2.80, 4.02, 4.19-4.31, 6.71, 6.82, 6.88-7.19, 6.93, 7.53, 7.61, 12.08

Comparative Example 3

4,4'-{4-fluoro-2-methyl-7-[(E)-2-{4-[4-(2,3,4,6-tetrafluorophenyl)butoxy]phenyl}vinyl]-1H-indole-1,3-diyl}dibutanoic Acid By the same procedure as in Example 47→Example 4→Example 8→Example 9 using diethyl 14,4'-(7-bromo-4-fluoro-2-methyl-1H-indole-1,3-diyl)dibutanoate (which was prepared by the same procedure as in Example 1→Example 2 using (2-bromo-5-fluorophenyl)hydrazine instead of (2-bromo phenyl)hydrazine hydrochloride) instead of the compound prepared in Example 10, and using the corresponding sulfonate instead of the compound prepared in Example 7, the comparative compound having the following physical properties was obtained.

TLC:Rf 0.44 (methylene chloride:methanol=9:1)
$^1$H-NMR (DMSO-D$_6$): δ 1.58-1.95, 2.12-2.24, 2.30, 2.65-2.80, 4.00, 4.26, 6.71, 6.82, 6.91, 7.04, 7.38-7.50, 7.52, 7.61, 12.07

Effects of the compound of the present invention of the formula (I) can be confirmed by the following experiments. Although the experimental methods are described below, the present invention is not limited thereto.

Biological Example 1

Effects of Compounds on LTD$_4$-Induced Increase in Intracellular Calcium Levels Chinese hamster ovary (CHO) cells expressing the human cysLT$_1$ receptor were seeded at a density of $0.4 \times 10^5$ cells/well into a 96-well plate and cultured in an F-12 medium at 37° C. in the presence of 5% CO$_2$ for 24 hours. The cells were incubated in the culture medium containing 7.5 μM Fura2-AM, 20 mM 2-[4-(2-hydroxyethyl)-1-piperazinyl]ethanesulfonic acid (HEPES) and 2.5 mM probenecid, at 37° C. for about 60 minutes. The Fura2-AM-loaded cells were washed once with assay buffer (Hank's buffer containing 20 mM HEPES), and the LTD$_4$-induced intracellular calcium influx was measured using a FDSS2000 (manufactured by Hamamatsu Photonics K.K.). The compounds of the present invention were applied 30 minutes prior to LTD$_4$ stimulation, and time-course changes of the response provoked by 100 nM of LTD$_4$ was measured over 150 seconds. The receptor antagonistic activity of the compounds of the present invention was evaluated in terms of a maximum fluorescence intensity obtained up to 150 seconds after LTD$_4$ stimulation, and a 50% inhibitory concentration (IC$_{50}$) was calculated for each compound.

As a result, the compounds of the formula (I) exhibited IC$_{50}$ values of 10 μM or less. For example, those compounds prepared in Examples 9, 9 (1), 11, 21 (1), 14 (2), 21 (2), and 14 (3) exhibited IC$_{50}$ values of 1.1, 1.5, 0.21, 0.16, 1.8, 0.24 and 7.0 nM, respectively.

Biological Example 2

Effects of Compounds on LTD$_4$-Induced Increases in Intracellular Calcium Levels HEK293 cells expressing the human cysLT$_2$ receptor were seeded at a density of $1 \times 10^5$ cells/well into a 96-well plate and cultured in a Dulbecco's Modified Eagle Medium (DMEM) at 37° C. in the presence of 5% CO$_2$ for 24 hours. The cells were incubated in the culture medium containing 7.5 μM Fura2-AM, 20 mM 2-[4-(2-hydroxyethyl)-1-piperazinyl] ethanesulfonic acid (HEPES) and 2.5 mM probenecid, at 37° C. for about 60 minutes. The Fura2-AM-loaded cells were washed once with assay buffer (Hank's buffer containing 20 mM HEPES), and the LTD$_4$-induced intracellular calcium influx was measured using a FDSS2000 (manufactured by Hamamatsu Photonics K.K.). The compounds of the present invention were applied 30 minutes prior to LTD$_4$ stimulation, and time-course changes of the response provoked by 100 nM of $LTD_4$ was measured over 150 seconds. The receptor antagonistic activity of the compounds of the present invention was evaluated in terms of a maximum fluorescence intensity obtained up to 150 seconds after $LTD_4$ stimulation, and a 50% inhibitory concentration ($IC_{50}$) was calculated for each compound.

As a result, the compounds of the formula (I) exhibited $IC_{50}$ values of 10 µM or less. For example, those compounds prepared in Examples 9, 9 (1), 11, 21 (1), 14 (2), 21 (2), and 14 (3) exhibited $IC_{50}$ values of 2.8, 6.6, 0.77, 2.1, 44, 2.9 and 15 nM, respectively.

Biological Example 3

Effects of Compounds on $LTD_4$-Induced Bronchoconstriction in Guinea Pigs

Guinea pigs were anesthetized by injection of pentobarbital sodium (75 mg/kg, i.p.), and a polyethylene cannula was inserted into the trachea which had been incised. For the purpose of administration of $LTD_4$, a catheter was inserted into the jugular vein of the animal. One side of the cannula inserted into the trachea was connected with a volume-controlled respirator to perform artificial respiration at a ventilation volume of 5 mL and at a ventilation rate of 70 times/min. $LTD_4$ was administered intravenously to induce the bronchoconstriction, and the airway resistance was measured using the Konzett-Rossler method. The bronchoconstriction response was measured for 10 minutes after $LTD_4$-challenge, and the ratio of bronchoconstriction response was determined and represented as a percentage of the maximal increase in insufflation pressure achieved by clamping off the trachea. In this connection, the compound of the present invention was orally administered 1, 2, 4, 8, 12, 18, 24, 36 and 48 hours prior to challenge by $LTD_4$. In the present Example, the bronchoconstriction inhibition ratio of greater than 95% was evaluated as complete inhibition of bronchoconstriction. Tables 4 and 5 below show the results for oral administration of test compounds 2 and 24 hours prior to challenge by $LTD_4$.

As a result, it can be seen that a ethynylindole compound having a triple bond represented by the formula (I) exhibits complete inhibition of the bronchoconstriction in guinea pigs, in case of oral administration. Furthermore, it was demonstrated that the triple-bond ethynylindole compound exhibits complete inhibition of the bronchoconstriction not only for the administration of the compound 2 hours prior to challenge by $LTD_4$, but also for the administration of the compound 24 hours prior to the challenge by $LTD_4$. For example, as shown in Table 4, the compounds of Examples 9, 14 (2), and 14 (3) exhibited complete inhibition of guinea pig bronchoconstriction, in case of oral administration. In Table 4, the parenthesized numeral represents a dose of the test compound, and the numerals within the table represent inhibition ratios (%).

TABLE 4

|  | Example 9 (1 mg/kg) | Example 14(2) (1 mg/kg) | Example 14(3) (1 mg/kg) |
|---|---|---|---|
| Administered 2 hours prior to $LTD_4$ challenge | 98.5 | 99.5 | 99.6 |
| Administered 24 hours prior to $LTD_4$ challenge | 99.2 | 98.9 | 98.1 |

Namely, it was demonstrated that the ethynylindole compound of the formula (I) is a compound having long-acting effects even upon oral administration, and is useful as an oral therapeutic agent for respiratory diseases.

In this connection, an inhibition ratio of bronchoconstriction was measured for administration of the same dose of ethenylindole compounds having a double bond of Comparative Examples 1 to 3, corresponding to the compounds of Table 4. As shown in Table 5 below, there was complete inhibition in some cases if administration of the compound was made 2 hours prior to challenge by $LTD_4$, but no complete inhibition was achieved if administration of the compound was made 24 hours prior to challenge by $LTD_4$. In Table 5, the parenthesized numeral represents a dose of the test compound, and the numerals within the table represent inhibition ratios (%).

TABLE 5

|  | Comparative Example 1 (1 mg/kg) | Comparative Example 2 (1 mg/kg) | Comparative Example 3 (1 mg/kg) |
|---|---|---|---|
| Administered 2 hours prior to $LTD_4$ challenge | 98.6 | 97.5 | 53.2 |
| Administered 24 hours prior to $LTD_4$ challenge | 74.1 | 43.2 | 16.1 |

Formulation Examples

Formulation Examples applied to practical use of the present invention are shown below.

Formulation Example 1

4,4'-[2-methyl-7-({4-[4-(pentafluorophenyl)butoxy]phenyl}ethynyl)-1H-indole-1,3-diyl]dibutanoic acid (100 g), calcium carboxymethyl cellulose (disintegrating agent, 20 g), magnesium stearate (lubricant, 10 g), and microcrystalline cellulose (870 g) were mixed in a conventional manner and compressed to obtain 10,000 tablets wherein each of the tablets contain 10 mg of the active ingredient.

Formulation Example 2

4,4'-[2-methyl-7-({4-[4-(pentafluorophenyl)butoxy]phenyl}ethynyl)-1H-indole-1,3-diyl]dibutanoic acid (200 g), mannitol (2 kg), and distilled water (50 L) were mixed in a conventional manner. Then the solution was filtered through a dust-proof filter, and then 5 ml aliquots were charged into ampoules. The ampoules were autoclaved to obtain 10,000 ampoules wherein each of the ampoules contain 20 mg of the active ingredient.

EFFECT OF THE INVENTION

The compound of the present invention of the formula (I) is a compound having superior long-lasting effects in combination with a potent $cysLT_1/cysLT_2$ receptor antagonistic activity, and is therefore very useful as a long-acting agent for treating respiratory diseases, in case of oral administration.

What is claimed is:

1. A compound of the formula (I):

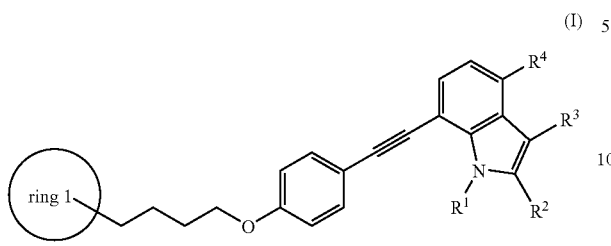

wherein:
R¹ represents a carboxymethyl group, or a 3-carboxypropyl group,
R² represents a hydrogen atom, or a C1-4 alkyl group,
R³ represents a [1-(carboxymethyl)cyclopropyl]methyl group, or a 3-carboxypropyl group,
R⁴ represents a hydrogen atom, or a halogen atom, and
ring 1 represents:

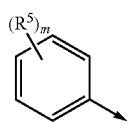

wherein R⁵ represents a C1-4 alkyl group, or a halogen atom, m represents 0 or an integer of 1 to 5, R⁵ may be the same or different when m is 2 or greater, and an arrow binds to a butyloxy group; or a salt thereof.

2. The compound according to claim 1, wherein ring 1 is

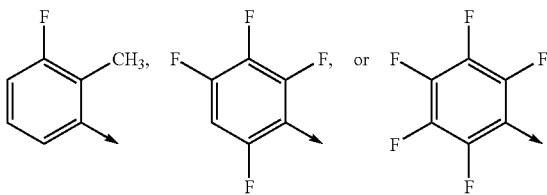

wherein an arrow has the same meanings as defined in claim 1.

3. The compound according to claim 2, wherein R¹ is a 3-carboxypropyl group and R³ is a 3-carboxypropyl group.

4. The compound according to claim 1, wherein the compound is
(1) 4,4'-[2-methyl-7-({4-[4-(pentafluorophenyl)butoxy]phenyl}ethynyl)-1H-indole-1,3-diyl]dibutanoic acid,
(2) 4,4'-[7-({4-[4-(3-chloro-2-methylphenyl)butoxy]phenyl}ethynyl)-2-methyl-1H-indole-1,3-diyl]dibutanoic acid,
(3) 4,4'-[2-methyl-7-({4-[4-(3,4,5-trifluorophenyl)butoxy]phenyl}ethynyl)-1H-indole-1,3-diyl]dibutanoic acid,
(4) 4,4'-[7-({4-[4-(3-fluoro-2-methylphenyl)butoxy]phenyl}ethynyl)-2-methyl-1H-indole-1,3-diyl]dibutanoic acid,
(5) 4,4'-[2-methyl-7-({4-[4-(2,3,4,5-tetrafluorophenyl)butoxy]phenyl}ethynyl)-1H-indole-1,3-diyl]dibutanoic acid,
(6) 4,4'-[2-methyl-7-({4-[4-(2,3,4,6-tetrafluorophenyl)butoxy]phenyl}ethynyl)-1H-indole-1,3-diyl]dibutanoic acid,
(7) 4,4'-[7-({4-[4-(4-fluoro-2-methylphenyl)butoxy]phenyl}ethynyl)-2-methyl-1H-indole-1,3-diyl]dibutanoic acid,
(8) 4,4'-[7-({4-[4-(4-fluoro-3-methylphenyl)butoxy]phenyl}ethynyl)-2-methyl-1H-indole-1,3-diyl]dibutanoic acid,
(9) 4,4'-[4-fluoro-2-methyl-7-({4-[4-(pentafluorophenyl)butoxy]phenyl}ethynyl)-1H-indole-1,3-diyl]dibutanoic acid,
(10) 4,4'-[7-({4-[4-(3-chloro-2-methylphenyl)butoxy]phenyl}ethynyl)-4-fluoro-2-methyl-1H-indole-1,3-diyl]dibutanoic acid,
(11) 4,4'-[4-fluoro-7-({4-[4-(3-fluoro-2-methylphenyl)butoxy]phenyl}ethynyl)-2-methyl-1H-indole-1,3-diyl]dibutanoic acid,
(12) 4,4'-[4-fluoro-2-methyl-7-({4-[4-(2,3,4,6-tetrafluorophenyl)butoxy]phenyl}ethynyl)-1H-indole-1,3-diyl]dibutanoic acid,
(13) [3-{[1-(carboxymethyl)cyclopropyl]methyl}-2-methyl-7-({4-[4-(pentafluorophenyl)butoxy]phenyl}ethynyl)-1H-indol-1-yl]acetic acid,
(14) (1-{[1-(carboxymethyl)-7-({4-[4-(3-chloro-2-methylphenyl)butoxy]phenyl}ethynyl)-2-methyl-1H-indol-3-yl]methyl}cyclopropyl)acetic acid,
(15) [3-{[1-(carboxymethyl)cyclopropyl]methyl}-7-({4-[4-(3-fluoro-2-methylphenyl)butoxy]phenyl}ethynyl)-2-methyl-1H-indol-1-yl]acetic acid, or
(16) 4,4'-[7-({4-[4-(pentafluorophenyl)butoxy]phenyl}ethynyl)-1H-indole-1,3-diyl]dibutanoic acid.

5. A pharmaceutical composition comprising the compound of the formula (I), according to claim 1 or a salt thereof, and a pharmaceutically acceptable carrier.

6. 4,4'-[2-methyl-7-({4-[4-(pentafluorophenyl)butoxy]phenyl{ethynyl)-1H-indole-1,3-diyl]dibutanoic acid or a salt thereof.

7. 4,4'-[4-fluoro-7-({4-[4-(3-fluoro-2-methylphenyl butoxy]phenyl{ethynyl)-2-methyl-1H-indole-1,3-diyl]dibutanoic acid or a salt thereof.

8. 4,4'-[4-fluoro-2-methyl-7-({4-[4-(2,3,4,6-tetrafluorophenyl)butoxy]phenyl{ethynyl)-1H-indole-1,3-diyl]dibutanoic acid or a salt thereof.

* * * * *

UNITED STATES PATENT AND TRADEMARK OFFICE
CERTIFICATE OF CORRECTION

PATENT NO.       : 8,115,014 B2
APPLICATION NO.  : 12/644378
DATED            : February 14, 2012
INVENTOR(S)      : Kazuyuki Ohmoto et al.

Page 1 of 1

It is certified that error appears in the above-identified patent and that said Letters Patent is hereby corrected as shown below:

Column 56, line 46 reads: "phenyl{ethynyl)-1H-indole-1,3-diyl]dibutanoic acid or a salt" should read --phenyl}ethynyl)-1H-indole-1,3-diyl]dibutanoic acid or a salt--.

Column 56, line 48 reads: "4,4'-[4-fluoro-7-({4-[4-(3-fluoro-2-methylphenyl" should read --4,4'-[4-fluoro-7-({4-[4-(3-fluoro-2-methylphenyl)--.

Column 56, line 49 reads: "butoxy]phenyl{ethynyl)-2-methyl-1H-indole-1,3-diyl]dibu-" should read --butoxy]phenyl}ethynyl)-2-methyl-1H-indole-1,3-diyl]dibu- --.

Column 56, line 52 reads: "rophenyl)butoxy]phenyl{ethynyl)-1H-indole-1,3-diyl]dibu-" should read --rophenyl)butoxy]phenyl}ethynyl)-1H-indole-1,3-diyl]dibu- --.

Signed and Sealed this
Twenty-first Day of August, 2012

David J. Kappos
*Director of the United States Patent and Trademark Office*